United States Patent
Trexler et al.

(10) Patent No.: US 11,268,125 B2
(45) Date of Patent: Mar. 8, 2022

(54) DEVICES AND ASSAYS FOR ESTIMATING MICROBIAL LOAD AND DIFFERENTIATING MICROBIAL POPULATIONS

(71) Applicant: Prolific Earth Sciences Corporation, Montgomery, NY (US)

(72) Inventors: E. Brady Trexler, Montgomery, NY (US); Judith Fitzpatrick, Montgomery, NY (US)

(73) Assignee: Prolific Earth Sciences Corporation, Montgomery, NY (US)

(*) Notice: Subject to any disclaimer, the term of this patent is extended or adjusted under 35 U.S.C. 154(b) by 58 days.

(21) Appl. No.: 16/840,042

(22) Filed: Apr. 3, 2020

(65) Prior Publication Data
US 2021/0310038 A1   Oct. 7, 2021

(51) Int. Cl.
*C12Q 1/06* (2006.01)
*G01N 15/02* (2006.01)

(52) U.S. Cl.
CPC ........... *C12Q 1/06* (2013.01); *G01N 15/0205* (2013.01); *G01N 2015/025* (2013.01)

(58) Field of Classification Search
None
See application file for complete search history.

(56) References Cited

U.S. PATENT DOCUMENTS

| | | | | |
|---|---|---|---|---|
| 5,935,804 A * | 8/1999 | Laine | ............ | C07K 14/001 435/18 |
| 6,165,740 A * | 12/2000 | Fukuda | ............ | C12Q 1/04 435/283.1 |
| 6,184,027 B1 * | 2/2001 | Laine | ............ | C07K 14/001 435/261 |
| 9,903,857 B2 | 2/2018 | Polwart | | |

(Continued)

FOREIGN PATENT DOCUMENTS

| | | |
|---|---|---|
| AU | 2005245777 | 4/2005 |
| GB | 2477752 | 8/2011 |
| KR | 1020150101649 | 9/2015 |

OTHER PUBLICATIONS de Vries et al., Soil Biol. Biochem., 38:2092-2103 (2006).*
(Continued)

*Primary Examiner* — David W Berke-Schlessel
(74) *Attorney, Agent, or Firm* — BakerHostetler

(57) ABSTRACT

Devices, methods, kits and means for easy, accurate, and fast estimation of soil microbial load, including fungal load, and fungal to bacterial ratio are described. The methods include extracting soil biomass into an extraction fluid to obtain a soil extract and detecting the fungal fraction, the bacterial fraction, and the fungal to bacterial ratio in the soil extract. The devices typically include microBIOMETER®, devices for particle size discrimination, and devices for absorbance and reflectance detection. The difference in microscopic sizes or spectroscopic absorbance of the fungal particles relative to those of the bacterial particles is used to compute (Continued)

the contribution of each type of particle to the biomass. In one example, the relative coverage of the microBIOM-ETER® device membrane by the fungal and/or bacterial particles can be measured by and then calculated using a cell phone camera and application.

26 Claims, 6 Drawing Sheets

(56) References Cited

U.S. PATENT DOCUMENTS

| | | | |
|---|---|---|---|
| 10,179,926 | B2 | 1/2019 | Fitzpatrick |
| 2009/0229179 | A1* | 9/2009 | Hafeel ............... C12Q 1/06 47/58.1 SC |
| 2014/0220623 | A1 | 8/2014 | Fitzpatrick |

OTHER PUBLICATIONS

Aleixo et al., Ciencia Rural, Santa Maria, 44(4):588-594 (2014) (Year: 2014).*
Chiu et al., Geoderma, 130:265-271 (2006) (Year: 2006).*
de Vries et al., Soil Biol. Biochem., 38:2092-2103 (2006) (Year: 2006).*
Ekelund et al., Soil Biol. Biochem., 33:475-481 (2001) (Year: 2001).*
Li et al., Biol. Fertil. Soils, 39:301-311 (2004) (Year: 2004).*
Findlay et al., Microb. Ecol., 43:55-66 (2002) (Year: 2002).*
Gong et al., Enviro. Pollut., 257(113485):1-11 (2020) (Year: 2020).*
Madsen et al., Ann. Occup. Hyg., 50(2):175-187 (2006) (Year: 2006).*
Miller et al., Cytometry, 11:667-675 (1990) (Year: 1990).*
Rousk et al., FEMS Microbiol. Ecol, 62:258-267 (2007) (Year: 2007).*
Seaton et al., Soil Biol. Biochem., 144(107766):1-10 (2020) (Year: 2020).*
Sessitsch et al., App. Enviro. Microbiol., 67(9):4215-4224 (2001) (Year: 2001).*
Wang et al., Acta Oecologica. 95:1-11 (2019) (Year: 2019).*
Zornoza et al., Appl. Soil Ecol., 42(3):315-323 (2009) (Year: 2009).*
Sakamoto et al., Soil. Fertil. Soils, 17:39-44 (1994) (Year: 1994).*
Anderson, et al., "A Physiological method for the Quantitative Measurement of Microbial Biomass in soils", Soil Biology and Biochemistry, 10(3):215-221 (1978).
Bailey, et al., "Fungal-to-bacterial ratios in soils investigated for enhanced C sequestration", Soil Biol. Biochem., 34: 997-1007 (2002).
Burggraaff, et al., "Standardized spectral and radiometric calibration of consumer cameras", Opt. Express, 27(14)19075-19101 (2019).
Ghassemi, et al., "Evaluation of Mobile Phone Performance for Near-Infrared Fluorescence Imaging", IEEE Trans Biomed Eng., 64(7):1650-1653 (2017).
Leck, "Preparation of Lactophenol Cotton blue Slide Mounts", Community Eye Health, 12(30):24 (1999).
Maurer-Spurej, et al., "Portable Dynamic Light Scattering Instrument and Method for the Measurement of Blood Platelet Suspensions", Phys. Med. Biol., 51(15):3747-3758 (2006).
McGonigle, et al., Smartphone spectrometers, Sensors, 18:223 (2018).
Ozer, et al., "Effect of some organic amendments on onion bulb rot", Phytoparasitica, 30(4):420-433 (2002).
Soares, et al., "Microbial growth and carbon use efficiency in soil: Links to fungal-bacterial dominance", SOC-quality and stoichiometry, Soil Biology and Biochemistry, 131:195-205 (2019).
Stahl, et al., "Sources of error in direct microscopic methods for estimation of fungal biomass in soil", Soil Biology and Biochemistry, 27(8):1091-1097 (1995).
Vierheilig, et al., "Ink and Vinegar, a Simple Staining Technique for Arbuscular-Mycorrhizal Fungi", Applied and Environmental Microbiology, 64(12):5004-5007 (1998).

* cited by examiner

DEVICES AND ASSAYS FOR ESTIMATING MICROBIAL LOAD AND DIFFERENTIATING MICROBIAL POPULATIONS

STATEMENT OF FEDERALLY SPONSORED RESEARCH

None.

FIELD OF THE INVENTION

The invention is generally directed to analysis of soil bacterial and fungal biomass in various media and generation of a fungal to bacterial ratio by easy and fast methods based on particle size and particle absorbance.

BACKGROUND OF THE INVENTION

Measurement of microbial biomass or other soil analytes is difficult because of the large amount of particulate matter that is irrelevant to the measurement of these analytes and because the color of an extract may preclude assaying for analytes by methods such as spectrophotometry, turbidity, nephelometry and visual comparison. One of the most difficult parameters to measure is Microbial Biomass, which is an excellent indicator of soil and compost quality and is a predictor of soil fertility. Microbial biomass is the source of the majority of the stored soil carbon (Miltner, A., Bombach, P., Schmidt-Brücken, B., Kästner, M., 2012. SOM genesis: microbial biomass as a significant source. Biogeochemistry 111, 41-55). As a result, it is an important indicator that carbon sequestration is occurring because if microbes do not increase, then carbon sequestration cannot increase. Soil microbes recycle the organic matter in soil and convert it into forms that can be utilized by plants. Bacteria represent the most numerous microbes in soil and serve as the bottom rung of the microbial soil food chain, which consists of Bacteria and Archaea, Protista, Fungi and microscopic Animalia such as nematodes. The Protista are present in much lower numbers than bacteria or fungi and the animalia such as nematodes which feed on the Protista, bacteria and fungi are in even fewer numbers. Abundant microbial life indicates that the nutrient levels of soil are sufficient and balanced and that there is an absence of significant levels of deleterious or poisonous substances such as heavy metals or high concentrations of salts.

Studies have revealed that microbial biomass is a predictor of soil fecundity and highly correlated with other predictors of fecundity such as organic carbon, soluble organic carbon, nitrogen, phosphorus and potassium and with crop yield in organic systems. However, tests and test standardization to establish the microbial content of soils are not extensively utilized in large part due to existing methods being expensive, having to be performed in a laboratory, and having poor performance. Since 1966, the gold standard for measuring total microbial biomass has been the chloroform fumigation (CF) assay which measures the amount of C or N in a soil sample before and after lysing the microbes with chloroform (Jenkinson. D. S. Studies on the decomposition of plant material in soil. II. Partial sterilization of soil and the soil biomass. 1966, Journal of Soil Science. 17 pp. 280-302). The CF assay was validated against microscopy, which before the development of digitized microscopy was incredibly labor intensive and subjective. CF does not distinguish between species and many are interested in the ratio of fungi to bacteria (F:B) as fungal populations have been shown to be very important in soil health; the sequestration of carbon in the soil (Soares, M., Rousk, J. 2019. Microbial growth and carbon use efficiency in soil: Links to fungal-bacterial dominance, SOC-quality and stoichiometry, Soil Biology and Biochemistry 131,195-205); suppression of soil fungal pathogens (Özer, N., Köycil N. D. Mirik, M., Soran, H., & Boyraz D. (2002). Effect of some organic amendments on onion bulb rot. *Phytoparasitica,* 30(4), 429-433); and maintenance of plant health (Roy-Bolduc A, Hijri M. (2011) The Use of Mycorrhizae to Enhance Phosphorus Uptake: A Way Out the Phosphorus Crisis. J Biofertil Biopestici:104).

It is generally reported that about half of the microbial biomass in agricultural fields is fungal and that the fungal biomass of forests can be orders of magnitude greater than the bacterial component. There is currently no gold standard for the measurement of Soil Fungal Biomass (SFB). Phospholipid fatty acid analysis (PLFA) estimates fungal biomass based on the amount of PLFA 18:2w6,9. This has several problems. First, this fatty acid is also found in gram negative bacteria, and second, PLFA does not measure fungal spores which can seriously affect results as spores can be numerous (Sharma M. P. Buyer J. S. 2005. Comparison of biochemical and microscopic methods for quantification of arbuscular mycorrhizal fungi in soil and roots. Applied Soil Ecology 95 86-89). Third, PLFA results from lab to lab can vary very significantly. The PLFA ratio of fungi:bacteria varies between 0.001 and 0.1 because of the very low amounts of fungal PLFA as opposed to bacterial PLFAs. Microscopic analysis ranges from less than 1 to about 20. A further problem for PLFA is the delicacy of fungi: for accurate analysis, samples should be frozen at −20° C. upon collection and mailed frozen for testing as dead fungi are not detected by PLFA. Mailing a frozen sample requires dry ice and two-day delivery which adds significantly to the cost and time for the analysis.

Soil Fungal Biomass (SFB) has traditionally been estimated by microscopy. This involves measuring hypha diameter and length, counting individual hypha and analyzing via conversion factors. This is time consuming, requires trained microscopists and is very dependent on the microscopist (Stahl, P. D., Parkin, T. B., & Eash, N. S. (1995). Sources of error in direct microscopic methods for estimation of fungal biomass in soil. *Soil Biology and Biochemistry,* 27(8), 1091-1097).

Anderson and Domsch (A Physiological Method for the Quantitative Measurement of Microbial Biomass in Soils. Soil Biology and Biochemistry Vol 10, No.3, 1978, 215-221) modified the substrate-induced respiration assay (SIR) (which differs very substantially from soil respiration assay called the Haney Test and a commercial version sold under the name SOLVITA®, (SOLVITa, LLC, St. Pete Beach, Fla.)) to measure SFB. The SIR test calculates $CO_2$ generated by soil microbial biomass to which is added a simple carbohydrate (usually glucose) using the formula, 1 ml of $CO_2$/hour=40 ug MBC/gram of soil. To calculate fungal biomass, bacterial respiration is inhibited (Anderson and Domsch Soil Biol Biochem. Vol. IO. pp. 215 to 221.). The total microbial biomass estimated by the SIR test correlates well with PLFA but the fungal component does not correlate. Anderson & Domsch state that SIR tests activity so does not measure the dormant population. They also stated that the fungal PLFAs are shared by other microbes and that the critical PLFAs are present in very different quantities in different soil fungi.

Measurement of fungal chemical components is not useful in estimating fungal biomass because the fungal chemicals glomalin, ergosterol and chitin all remain in the soil long after the fungi have died. Baldrian et al (Estimation of fungal biomass in forest litter and soil. Fungal Ecology 6 (2013) 1-11) compared ergosterol, PLFA and PCR for estimating fungal biomass activity in forest soil and found estimates varied more than three-fold, concluding that the estimates of fungal biomass obtained with different biomarkers are not exactly comparable.

The medical field has developed assays for the identification of and medical diagnosis of fungal infections but none of these appear applicable to a rapid test for soil fungi quantitation.

A simple device for measurement of total microbial biomass in soil is described in U.S. Pat. No. 10,179,926, issued Jan. 15, 2019 to Prolific Earth Sciences Corporation.

There remains a need for easy, accurate, and fast estimation of the fungal fraction in the soil microbial biomass, that can be implemented in both laboratory and field settings, because fungi are critically important to plant and soil health.

Therefore, it is the object of the present invention to provide methods and devices for easy, accurate, and fast estimation of soil microbial load, including a method for fast estimation of the fungal fraction in the soil microbial biomass.

SUMMARY OF THE INVENTION

A method for measuring the bacterial and the fungal fractions of a soil microbial biomass is provided. The method typically includes the steps of extracting fungi and bacteria from the soil into a soil extract and detecting the fungal and bacterial fractions, and fungal to bacterial ratio in the soil extract using particle size and/or particle absorbance. Generally, the fungi and bacteria are extracted from the soil sample into an extraction fluid containing releasing agents such as sodium chloride, calcium chloride, and, optionally, a surfactant.

The soil extract may then be applied to a microscope slide, membrane or filter, or a transparent device such as a cuvette that is used in a spectrophotometer or colorimeter, then optically determining the total biomass, as well as the fungal fraction and the bacterial fraction of the biomass.

Once extracted into a soil extract, the particles in the soil extract may be detected with methods distinguishing the particles based on particle size and/or based on particle absorbance. Typically, the soil extract includes particles of different sizes and surface areas. The methods may include testing the soil extracts to detect particles of two sizes: bacteria with a particle size between about 0.5 $\mu m^2$ and about 10 $\mu m^2$ and/or fungal particles with size between about 10 $\mu m^2$ and about 800 $\mu m^2$. The methods may include obtaining a total surface for each group of particles in a sample and then calculating the ratio between the two surface areas to obtain the fungal to bacterial ratio.

In one example, the fungi are identified microscopically as those organisms larger than 10 $\mu m^2$ and bacteria are identified as those organisms less than or equal to 10 $\mu m^2$ and the fungal to bacterial ratio is determined by the ratio of the total area of the fungi to the total area of the bacteria.

The particle size may be determined by any suitable method configured for particle size determination. Suitable methods for particle size determination include light microscopy, fluorescent microscopy, flow cytometry, particle counting, dynamic light scattering, and laser diffraction.

The fungal to bacterial ratio of the biomass may also be determined colorimetrically on a membrane or filter or in a cuvette with the absorbance of soil-colored bacteria and fungi differing in different light spectra, such as in the red and blue spectra. The methods utilizing particle absorbance typically include using equation 1:

$$R = a - (a^2/b) \qquad \text{(equation 1)};$$

where:
R is fungal to bacterial ratio;
a is particle absorbance at a light wavelength between about 500 nm and about 750 nm, such as between about 600 nm and 650 nm; and
b is particle absorbance at a light wavelength between about 400 nm and about 500 nm.

The microbial biomass of microorganisms that are not colored by soil pigments or other colored media may be detected by a staining procedure and then distinguished between bacteria and fungi based on the different stains. The fungal to bacterial ratio may then be determined colorimetrically or fluorescently using microscopy, flow cytometry, membrane capture devices, and spectrometry.

Devices and systems useful for fungal to bacterial ratio determination based on particle absorbance or color include the microBIOMETER® described in U.S. Pat. No. 10,179,926 issued to Prolific Earth Sciences Corporation. Examples demonstrate an excellent correlation with both methods of optically distinguishing the organisms. Other devices include spectrophotometers, such as ultraviolet to visible spectrometers and fluorescence spectrometers.

The systems may be automated for use in the field, with a cell phone application providing the analysis via the camera function.

The system has also been automated for use in the laboratory providing the analysis via digital microscopy.

BRIEF DESCRIPTION OF THE DRAWINGS

FIG. 1A is the original image of the soil extract after processing of the sample. FIG. 1B is the image after it has been segmented into individual contiguous particles, with adjacent particles in different intensities. The area of each particle was determined by the area of the polygon that circumscribed it, or more simply by the number of pixels it consumed. Both methods produced similar results.

DETAILED DESCRIPTION OF THE INVENTION

I. Definitions

The terms "fluid" or "aqueous fluid" refers to a fluid containing between about 75% and 99% water. Suitable waters of the aqueous fluid include stream water, tap water, purified water, filtered water, deionized water, or distilled water.

The term "extraction fluid", refers to a solution containing salts and detergents in a concentration optimized to release microbes without destroying them during the time required for assay. The extraction fluid may be provided in liquid form in a tube or as a tablet or powder to be added to water. Extraction fluid may contain preservatives such as sodium azide and or other constituents for quality control.

As used herein, the term "extracted soil sample" refers to the extraction fluid containing microorganisms extracted from the soil sample placed therein.

The term "microbes" or "microorganisms" refers to microscopic organisms such as bacteria, fungi, algae and protozoa.

The terms "microbial biomass" or "microbial content" refer to all of the microorganisms in a given habitat.

The term "whisking" refers to treating the extraction soil solution to mechanical agitation that assists in releasing microbes in extraction fluid from soil particles, but is not so vigorous as to disrupt the microbes or to pulverize soil particles so that they will not precipitate during the settling process, e.g. sonication creates soil particles that remain in extraction fluid during settling.

The term "colored microbes" refers to the color possessed by microbes due to ingested soil particles and pigments.

The term "bacterial" refers to both bacterial and archaebacterial Domains. The term "Fungal" does not imply any distinction between fungal forms.

Figure 4A:
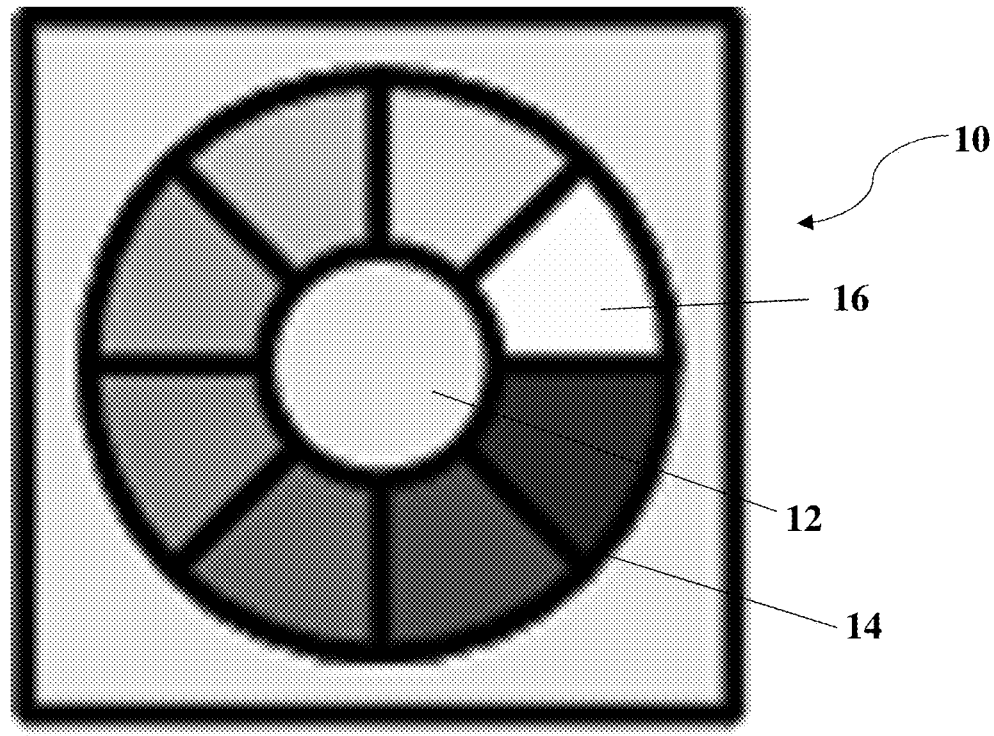
FIG. 4A is a diagram of an exemplary device for retaining microbes from soil extract. The device 10 is a test card containing a sample application site 12 and color scale disk or gray scale disk 14. The disk 14 is separated into individual comparators 16.

The term "test card" refers to the device described in U.S. Pat. No. 10,179,926, and an exemplary test card is shown in FIG. 4A.

The terms "window" or "sample window" refer to the membrane exposed portion of the "test card" that is surrounded by a color comparator.

The terms "comparator" or "color comparator" refers to one of a series of grayscale or colored reference images that are used on a color or grayscale strip to standardize colorimetric or spectrosphotometric readings in various lighting conditions or on different imaging setups.

The terms "microBIOMETER", "microBIOMETER®", "MICROBIOMETER", and "MICROBIOMETER®" refer to the testing device, process, and kit as defined in U.S. Pat. No. 10,179,926 that measures microbial biomass (MB) as well as to the testing device and process as defined herein that measures microbial biomass and the fungal and bacterial contributions to that microbial biomass.

Recitation of ranges of values herein includes each separate value falling within the range, unless otherwise indicated.

Use of the term "about"is intended to describe values either above or below the stated value in a range of approximately +/− 10%; in other aspects the values may range in value either above or below the stated value in a range of approximately +/− 5. The preceding ranges are intended to be made clear by context, and no further limitation is implied.

II. Soil Samples and Processing for Analysis

A. Soil Samples

The soil samples include solid soil, which may be dried, field moist, or wet soil. Soil samples containing an earthy mix of minerals, air, water, and organic matter can be used. Soil samples can be liquids, such as compost extract or compost tea. Typically, soil samples compose 5-20% of the testing reaction volume.

Composted organic matter and humus is a predominant component of the nutrient content of soil. Because solid compost is heavy and requires spreading for use as a fertilizer, many who use compost as fertilizer prefer to extract the nutrients and microbes in compost into water and apply the soluble compost extract by spraying. This is basically the only feasible method of applying this nutrient to growing fields. Solubilized compost sprayed directly onto plants can also have pesticidal activity, which is attributed to the microbial content, thus eliminating or diminishing the need for commercial pesticides. Compost extract can be fortified with other nutrients or microbes ("compost tea") or diluted according to the requirements of the target crop. In some applications, methods for measuring the microbial content of soils can be used to determine the optimal concentration of solubilized compost for application to target crops. For example, solubilized composts can be diluted or concentrated from several billion parts/ml up to a million parts/mL, or less than a million parts per mL, based upon the microbial content of the sample. The concentration of microbes can be used to determine the dilution factor that should be used for spraying of the extract or tea. It is also useful for evaluating compost extract conditions for optimal microbial content and nutritional additives used to increase microbial population of a compost extract.

B. Soil Microbes Including Fungi

Microbial life within the soil is a key factor in enhancing plant growth. Typically, the microbial biomass of a soil correlates with the ability of a soil to support the growth of plants. Soil microbes play an important role in the physical and chemical formation of soils. Soil microbes exude a glue that allows them to cling to soil particles and which also gives the clumpy structure to soil. This clumpy structure is a critical component of soil health as it retards erosion, provides aeration, and increases water holding capacity of the soil. Microbes convert soil nutrients into forms that can be used by plants, control pathogens and bind the soil making it capable of retaining water and air. The microbial food chain in soil has been linked to crop yield and the presence of microbes within soil can be used as a marker for soil quality and fertility. At the bottom of the food chain are bacteria that provide food for protozoa like paramecia and amoeba, which are in turn grazed upon by nematodes that then feed larger animals such as earth worms and insects. In this process of grazing on bacteria which are rich in organic nitrogen, ammonia and nitrates are released for use by plants.

1. Soil Bacteria

Bacteria are single-celled prokaryotic organisms, typically 1-8 micrometers in length. One gram of healthy soil typically contains $10^6$ to $10^8$ bacteria. The number of species of bacteria per gram of soil has been estimated as between 2000 and 8.3 million (Gans, et al., Science, 309:1387-1390 (2005); Schloss and Handelsman, *PLoS Comput Biol.*, 2(7): e92. (2006)). The most abundant bacterial groups in soil samples from the Western Hemisphere were the Bacteroidetes, Betaproteobacteria and Alphaproteobacteria (Roesch, et al., *ISME J.*, 1:283-290 (2007)). Exemplary soil bacteria include *Nitrosomonas* spp., *Nitrobacter* spp., *Rhizobium* spp., *Bradyrrhizobium* spp., *Azotobacter* spp, *Bacillus* spp., *Azotobacter* spp., *Micrococcus* spp., *Achromobacter* spp., *Nitrosococcus* spp., *Pseudomonas* spp., *Serratia* spp., *Xanthomonas* spp. and *Clostridium,*spp.

Bacteria are responsible for biochemical transformations within soil and directly or indirectly provide nutrients for plant life. In return, up to 30-50% of the nutrition the plant sends to the root is released into the soil to support local microbial communities. This relationship is reciprocal: the plant feeds the microbes, the microbes feed the plant. It has now been demonstrated that the microbial biomass in the plant area is a critical indicator of the plant /health/metabolism: soil around roots of plants that are dying or going to seed have dramatically lower microbial load than their healthy counterparts.

Important biochemical processes carried out by soil bacteria include ammonification (i.e., protein to ammonia), nitrification (i.e., ammonia to nitrites, to nitrates), denitrification (i.e., release of free elemental nitrogen) decomposition of cellulose and other carbohydrates, the symbiotic and non-symbiotic fixation of atmospheric nitrogen, as well as the oxidation and reduction of iron and sulfur compounds.

Bacteria also contribute to compost fertility by preventing pathogens through the production of bacteriocins and antibiotics, as well as by competition.

Other microorganisms present in the soil sample include actinomycetes, fungi, algae, and protozoa. The soil microorganisms are discussed extensively by Sylvia et al. "Principles and Applications of Soil Microbiology." Upper Saddle River: Prentice Hall, N.J., (1998). 2. Soil Fungi A fungus is any member of the group of eukaryotic organisms that includes microorganisms such as yeasts and molds, as well as the more familiar mushrooms. Similar to animals, fungi are heterotrophs; they acquire their food by absorbing dissolved molecules, typically by secreting digestive enzymes into their environment. Fungi do not photosynthesize. Growth is their means of mobility, except for spores (a few of which are flagellated), which may travel through the air or water. Fungi are the principal decomposers in ecological systems. These and other differences place fungi in a single group of related organisms, named the Eumycota (true fungi or Eumycetes). Abundant worldwide, most fungi are inconspicuous because of the small size of their structures, and their cryptic lifestyles in soil or on dead matter. Fungi include symbionts of plants, animals, or other fungi and also parasites. They may become noticeable when fruiting, either as mushrooms or as molds.

At least 70,000 distinct species of soil fungi have been identified worldwide. These can be divided taxonomically into four groups: Zygomycota, Ascomycota, Basidiomycota, and Deuteromycota.

Fungi perform an essential role in the decomposition of organic matter and have fundamental roles in nutrient cycling and exchange in the environment. Saprophytic fungi are decomposers. Fungal saprophytes decompose cellulose and lignin found in soil for energy. The metabolic byproducts of this process include carbon dioxide, or $CO_2$, and small molecules such as organic acids; some of these metabolites can remain in the surrounding soil for thousands of years under the right conditions.

Mutualistic fungi are also called mycorrhizal fungi. These soil fungi colonize plant roots and are termed "mutualistic" because the fungi derive a benefit from the presence of the plants and vice versa. In exchange for carbon atoms from the plant, mycorrhizal fungi help make phosphorus easier for the plants to draw in, and they also bring other soil nutrients, including nitrogen, micronutrients and water to the plants on which they are anchored.

Mutualistic fungi include two major groups. One of these is the ectomycorrhizae, which grow on the surface of plant roots and are frequently seen on or near trees. The second major group, the endomycorrhizae, grow within, rather than on, the plant root cells, and are usually associated with grasses, crops grown in rows, vegetables and everyday shrubs.

They have long been used as a direct source of human food, in the form of mushrooms and truffles; as a leavening agent for bread; and in the fermentation of various food products. Since the 1940s, fungi have been used for the production of antibiotics, and, more recently, various enzymes produced by fungi are used industrially and in detergents. Fungi are also used as biological pesticides to control weeds, plant diseases and insect pests. Many species produce bioactive compounds called mycotoxins, such as alkaloids and polyketides, that are toxic to animals including humans. Losses of crops due to fungal diseases or food spoilage can have a large impact on human food supplies and local economies.

Up to 5 m of living hyphae of mycorrhizal fungi can be extracted from 1 g of soil. The four groups of mycorrhizal fungi are arbuscular, ectomycorrhizal, ericoid and orchid. Vesicular Arbuscular mycorrhiza (VAM) are the most common form of mcorrhiza, especially in agricultural plant associations.

Fungi are abundant in soil, but bacteria are more abundant. Fungi are important in the soil because of their beneficial symbiotic relationships with plants, as primary degraders of raw cellulosic material, as inhibitors of pathogens and as food sources for other, larger organisms. Soil fungi can be split into two groups based on their relationship to plants. Mycorrhiza are fungi that are intimately connected to and dependent upon the plant for their survival. Mycorrhiza increase the root area of a plant and are critical to the plant's access to water and mineral nutrients. The non-mycorrhizal fungi function to break down cellulosic materials, making the degradation products available to bacteria. These are most active when there is an abundance of material for digestion. Fungi are classified into species based primarily on the size, shape and color of their reproductive spores, which are used to reproduce. Most of the environmental factors that influence the growth and distribution of bacteria also influence fungi. The quality as well as quantity of organic matter in the soil has a direct correlation to the growth of fungi, because most fungi consume organic matter for nutrition. Fungi thrive in acidic environments, while bacteria do not thrive in acid, which results in an abundance of fungi in acidic areas. Fungi also grows well in dry, arid soils because fungi are aerobic, or dependent on oxygen, and the higher the moisture content in the soil, the less oxygen is present for them.

The soil fungi are extensively described in Teaming with Microbes by Jeff Lowenfels and Wayne Lewis (2010 Timber Press, Portland, Oreg.). Soil fungi are of two main types, mycorrhizal and saprophytic.

a. Mycorrhizal Fungi

Mycorrhizal fungi, (MF), which include the arbuscular mycorrhizal fungi (AMF), are symbionts of approximately 90% of land plants. Plants provide food for the AMF in carbon-rich molecules and AMF provide minerals (e.g. N, P, K, Mn, Mg, Cu, Zn) to the plants. AMF intimately interact with the plant roots via arbuscules and intraradical filaments, which are structures involved in exchange of nutrients and water between plant and fungus. MF also coat the root with a fungal hyphal net that substantially increases the surface area of the root and therefore increases the soil and nutrients to which the root has access. MF can also form extraradical filaments that extend from plant to plant forming a soil network that links many plants together, thus allowing the sharing of information and nutrients among plants. AMF do not grow independently of plant roots: they reproduce by spores that must find a root shortly after entering the vegetative state. Plants actually secrete substances that attract AMF.

Symbiosis with AMF provides the following benefits:
promotion of vegetative growth (Meddad-Hamza A., Beddiar A., Gollotte A., Lemoine M.C., Kuszala C. and Gianinazzi S., 2010. Mycorrhizal fungi improve the growth of olive trees and their resistance to transplantation stress. African Journal of Biotechnology Vol. 9(8), pp. 1159-1167);

increase of plant nutritional level (Hamed, A. A., Abdel Latef A., Chaoxing H. 2011. Effect of arbuscular mycorrhizal fungi on growth, mineral nutrition, antioxidant enzymes activity and fruit yield of tomato grown under salinity stress. Scientia Horticulturae 123:3 pp 228-233);

increase of the ability of plants to acquire nutrients (Hart, M. M. Forsythe J.A. 2012 Using arbuscular mycorrhizal fungi to improve the nutrient quality of crops; nutritional benefits in addition to phosphorus. -Scientia Horticulturae, Vol 148, pp 206-214);

improvement of the soil structure and aggregate stability (Piotrowski, J. S., Denich, T., Klironomos, J. N., Graham, J. M., & Rillig, M. C. 2004. The effects of arbuscular mycorrhizas on soil aggregation depend on the interaction between plant and fungal species. New Phytologist, 164(2), 365-373).

sequestration of carbon in soil (Wilson G. W. T., Rice, C. W., Rillig M. C., Springer A., Hartnett D. T.2009 Soil aggregation and carbon sequestration are tightly correlated with the abundance of arbuscular mycorrhizal fungi: results from long-term field experiments. Ecology Letters 12(5) Pages 452-461);

increase in resistance to drought and heavy metal contamination (Lin, A. J., Zhang, X. H., Wong, M. H., Ye, Z. H., Lou, L. Q., Wang, Y. S., & Zhu, Y. G. 2007. Increase of multi-metal tolerance of three leguminous plants by arbuscular mycorrhizal fungi colonization. Environmental Geochemistry and Health, 29(6), 473-481);

increase in soil microbial resistance to disease (Hohmann, P., & Messmer, M. M. (2017). Breeding for mycorrhizal symbiosis: focus on disease resistance. Euphytica, 213(5), 113).

The ability to detect root colonization by AMF rapidly and for low cost would a valuable tool, as many seeds are sold coated with AMF species that have been shown to increase yield and or disease and stress resistance of the plant. There is a large and growing market of companies selling AMF species that can be applied to seeds or growing root systems. These AMF are especially important for annual plants, because the fungal network from previous growing seasons may be absent. These AMF amendments are expensive and must be applied early in the plant's establishment. Additionally, the efficacy of any amendment treatment is highly dependent on matching the AMF species with the plant species, using the proper concentration, as well as soil edaphic and climactic conditions. Under optimal conditions, AMF amendments have demonstrated the ability to dramatically improve yield, quality and resistance. Purchasers of these amendments invest in expensive testing to confirm AMF colonization and to measure the extent of colonization via a fungal to bacterial ratio. Traditionally this is done via microscopic analysis by staining the root and or by counting the fungal spores associated with the root rhizosphere soil. These expensive tests require sending the sample to a lab, which can destroy the fungus en route, as it is delicate, and results are not available for at least a week. If an AMF application did not successfully colonize the roots, the reapplication should take place immediately, so time is of the essence.

Mycorrhizal fungi, (MF), which include the arbuscular mycorrhizal fungi (AMF), are symbionts of approximately 90% of land plants. The test for F:B ratio can be used to detect AMF by selecting soil containing roots. A root mass can be collected and after gently removing chunks of dirt, the actual root can be shaken to collect soil closely adhering to the root. This soil will contain microscopic rootlets that may be colonized by AMF. If colonized, the extraction of this soil to generate a soil MB extract will contain fungal spores as well as the rootlet-associated AMF which resemble grape clusters and appear dark and earth colored when viewed under a microscope.

b. Saprophytic Fungi

The saprophytic fungi are not restricted to the rhizosphere and function to break down plant material making the nutrients available to the next crop and to the soil food web (pathogenic fungi are considered saprophytic). These fungi multiply when presented with digestible foods. They are larger in diameter than the AMF and are found in the soil outside the rhizosphere; for example, soil collected about 4 inches from the plant stem and not rich in roots. These are the fungi that form mushrooms. They are detected in the same manner as described for AMF. microBIOMETER® does not distinguish between mycorrhizal and saprophytic fungi. However, the areas in which these two species reside is generally different and informative.

3. Algae

Algae can be split up into three main groups: the Cyanophyceae, the Chlorophyceae and the Bacillariaceae. The Cyanophyceae contain chlorophyll, which is the molecule that absorbs sunlight and uses that energy to make carbohydrates from carbon dioxide and water and also pigments that make it blue-green to violet in color. The Chlorophyceae usually only have chlorophyll in it which makes it green, and the Bacillariaceae contain chlorophyll as well as pigments that make the algae brown in color. 4. Protozoa Protozoa are eukaryotic organisms that were some of the first microorganisms to reproduce sexually, a significant evolutionary step from duplication of spores, like those that many other soil microorganisms depend on. Protozoa can be split up into three categories: flagellates, amoebae and ciliates.

C. Mycorrhizal Fungi

Mycorrhizal fungi, (MF), which include the arbuscular mycorrhizal fungi (AMF), are symbionts of approximately 90% of land plants. The test for F:B ratio can be used to detect AMF by selecting soil containing roots. A root mass can be collected and after gently removing chunks of dirt, the actual root can be shaken to collect soil closely adhering to the root. This soil will contain microscopic rootlets that may be colonized by AMF. If colonized, the extraction of this soil to generate a soil MB extract will contain fungal spores as well as the rootlet-associated AMF which resemble grape clusters and appear dark and earth colored when viewed under a microscope.

D. Obtaining Samples and Processing for Analysis

1. Obtaining Soil Sample

Samples of solid soil can be collected and measured in the field using a soil collection device and/or measuring cup or a 3 ml syringe modified for use as a punch with plunger which allows measurement of soil volume by the gradations on the syringe, and direct insertion of sample into the reaction vial. For example, multiple samples of equal volume are taken across a certain area and combined in a clean mixing vessel to produce a composite sample. In another embodiment, a sample is obtained by inserting a collection device into a batch of solid compost or soil. Sieving through a 2-5 mm sieve may be required to remove roots and rocks and other solid material that could adversely affect the integrity of the sample and impact results.

Solid soil samples can be measured using a collection vessel of a known volume. In one embodiment, solid soil is packed into a measuring vessel, such as a cup washer, to a volume of 0.210 ml. Alternatively, a punch with a plunger and a defined volume can be used to deliver between 0.2 and 1 cc of sample. Measurement of sample by volume corrects for soil water content. The volume of the cup washer is 0.21 ml, i.e., it holds 210 microliters of water. A soil sample can hold more than 2× dry weight of soil before volume changes.

Measuring volume compensates for water content of sample. The sample can hold more than 2× dry weight of soil before volume changes.

Solid and liquid samples are placed into a clean reaction vial. Solid samples that have been measured in a measuring cup can be transferred into the vial within the cup. Samples taken by punch can be directly delivered into the reaction vial by depressing the plunger. Liquid samples that have been measured using a pipette or the cap of the reaction vial can be introduced into the vial by removing 2 ml from the vial and measuring 2 ml of the compost extract into the vial.

Soil samples are solubilized within a reaction vessel or vial. For example, the tube has a diameter of 17 millimeters and a length of 120 millimeters and holds a volume of 15 mL. In other forms, the tube is sized to contain a volume of more than 15 mL, such as 50 mL, or more than 200 mL. An exemplary reaction vial is a polypropylene screw-cap vial, such as a conical centrifuge tube (e.g., Corning Life Sciences product No.: 352097). In some forms, the cap of the vial is threaded to seal the entire circumference of the vial. The cap of the reaction vial can hold a volume of 1 or 2 mL, or more than 2 mL when completely filled. In a particular form, the reaction vial is made of a hydrophobic material with an inert inner surface and the reaction vial is transparent to facilitate visual inspection of the contents. The outer face of the vial can contain graduated marks to enable visual estimation of the volume of fluid within the vial. The reaction vial should be clean and free from microbial contaminants.

Devices for mixing soil solutions by agitation or shaking are commercially available from multiple sources. Commercially available portable battery-operated shakers, such as the "Robart shaker" are useful in the field. The battery operated version of the Robart shaker is small and incorporates easily into a portable field kit. Other commercially available shakers, such as those suitable for shaking small paint or nail polish samples, can also be used.

Electrically powered laboratory equipment for mixing fluids, such as the Vortex mixer, and ultrasonic equipment such as sonicators are useful in the laboratory setting. A preferred device is a milk frother with the tip removed and replaced by a plastic tube coating the wand so that the wand reaches the bottom of the reaction vial—usually a requirement to ensure that the total volume of soil added to the reaction vial is whisked. Another method is to use of a battery operated vibrating wand, such as can be constructed using an ORAL® B children's tooth brush base with a plastic straw attached for penetrating the reaction vial.

2. Releasing Microorganisms into Extraction Fluid

Release of microbes from the soil sample into the extraction fluid occurs due to the action of releasing agents as well as due to mechanical agitation of the soil sample in the extraction fluid.

Soil samples are solubilized within the reaction vial by addition of water and/or an extraction fluid, followed by physical agitation to release soil-associated microbes into solution. The extraction fluid contains releasing agents, and may optionally contain clarification agents, preservatives, and/or anti-foaming agents. The amount of releasing agent, preservative, clarification agent or anti-foaming agent added to a soil sample can vary depending on the nature of the soil sample and the desired results. 10 ml of extraction fluid is capable of releasing ½ to 2 ml of soil or 1-4 ml of compost extract.

The biomass of a soil sample is suspended in the extraction fluid of the extracted soil sample as described in U.S. Pat. No. 10,179,926, the teachings of which are incorporated herein. Not all microbes are released during the process, but the amount of microbes released is orders of magnitude greater than that used for standard microscopic analysis, enabling the high reproducibility of the methods of analysis of extraction fluid by test card, microscopy, flow cytometry and spectrophotometry. The amount released is consistent from extraction to extraction and generates results consistent with microbial biomass estimated by other methods. The extracted organisms as verified by microscopy consist of fungi in ribbon or grape like clumps, bacteria, amoeba and other protozoa and various spores including fungal spores. The extraction fluid does not contain measurable amounts of actinomycetes. Releasing agents enable or enhance the solubilization of microbes within a soil sample by increasing dissociation of the microbes from soil particles. Releasing agents should not cause extensive foaming of the solution. Releasing agents for use in the methods are non-toxic and do not affect the visualization or measurement of microbes within the time required for analysis or for up to several hours afterward. In addition, releasing agents may be stable for extended periods of time and can be packaged and stored in a ready-to-use form. Releasing agents can be provided in premeasured ready-to-use form or packaged as a tablet or powder that when added to a set volume of water produce an extraction fluid. Tablets may alleviate the requirement for preservatives and the restrictions on transport of fluid. Tablets/powder must provide reagents that can be solubilized within the whisking time.

Extraction of microbes is very sensitive to the following variables: the concentration of salts and detergent, the time of whisking and the settling time. In a preferred embodiment, the assay is optimized to allow the least variation in extraction with variation of the variables. Typically, the releasing agents include inorganic salts and detergents.

For example, the releasing agents can include NaCl, KCl, $CaCl_2$, $MgCl_2$, and detergents, such as a sodium dodecyl sulfide (SDS). In the preferred embodiment, the extraction fluid contains a non-liquid detergent. In a preferred embodiment, the extraction fluid contains between about 0.3 and 10% NaCl, between about 3-5% CaCl, and between about 0.001% to 0.5% of a polysorbate-type nonionic surfactant. In the most preferred embodiment, the extraction fluid for extracting microbes up to 100 µm in size is 10.8% NaCl, 2.2% CaCl2, 0.001%SDS.

Mild detergent releasing agents are preferred. Exemplary detergents include blends of polyether-polymethylsiloxane-copolymer and nonionic surfactant, or polyether modified polysiloxane (CAPSIL®), TWEEN®® 20, TWEEN®® 80, also referred to as polysorbate 20 or 80, dioctanoylphosphatidyl choline and polyethylene-polypropylene glycol. In one embodiment, the releasing agent is either 0.1% TWEEN®® 20 or CAPSIL®. CAPSIL® can be a liquid at a 0.1%, 1%, 10%, 50% or 100% formulation in a dispensing vial. A particular test concentration of CAPSIL® is 0.2%.

The reagents may be provided in preformed premeasured liquid form, or in premeasured tablet or powder form ready to be diluted with predetermined volume of water. In the premeasured powder form, a dry detergent such as SDS is used.

Solubilized soil samples containing humic acid can be dark brown in color. Unless it is a very high concentration, humic acid and other pigments do not affect the quantitative measurement of microbes on the membrane because humic acid does not bind to the fiberglass membrane and is too small to be retained on the surface of the membrane. Should a pigment be present in sufficient quantity to color the entire membrane, it should color the quality control window and alert the tester to the interference. It is possible to subtract the intensity of the quality control window from the intensity of the sample window.

Clarifying agents may neutralize the pigmentation of soluble soil samples to facilitate accurate measurements of turbidity, reflectance and/or transmittance. Preferred clarifying agents for use in the methods do not affect the visualization or measurement of microbes within the time required for analysis or for several hours afterward. Exemplary clarifying agents in some conditions include hydrogen peroxide, chlorine dioxide, or mixtures of sodium hypochlorite, sodium chloride, sodium carbonate, sodium hydroxide and sodium polyacrylate (i.e., CLOROX® Regular Bleach). Numerous clarifying agents are commercially available. Typically, clarifying agents do not cause any damage to microbes in the time it requires to perform the methods and measurements of the test.

A preferred process for obtaining and extracting biomass from soil is described in U.S. Pat. No. 10,179,926, which separates soil microbes from non-living soil particles, generating a "soil MB extract". In particular, this procedure involves:

packing a volume of 0.5 cm3 (½ cc) of 2-4 mm sifted moist soil into a microBIOMETER ® soil sampler;

adding this to the solubilized microBIOMETER ® extraction powder mixture;

whisking with the microBIOMETER ® whisker for 30 seconds;

Allowing the mixed soil and extraction fluid to settle for 10-20 minutes, during which time the non-living soil particles precipitate, leaving a fluid on top of the settled particles that is greater than 95% microbes as determined by microscopy.

III. Measuring Microbial Biomass, Fungal Biomass and Fungal to Microbial Ratios

Devices and methods provide accurate and fast determination of fungal to bacterial ratios in a soil sample and reliably represent the fungal to bacterial ratios in a biomass as may be measured by standard laboratory techniques using staining and microscopy. The methods are easy to perform in the field, and may be more advantageous than laboratory methods such as Soil Fungal Biomass (SFB) or phospholipid fatty acid analysis (PLFA) for field applications. These laboratory methods are particularly challenging as fungi rapidly deteriorate after sampling.

Typically, the methods detect the fungal to bacterial ratios at ratios between about 0.1:1 and about 10:1, such as between about 0.5:1 and about 6:1, or about 1:1 and about 4:1.

The devices and methods relying on particle size or on particle absorbance are easily adaptable to be used separately or together. A sample from a soil extract may be used in an analysis based on particle size and then another sample from the same soil extract may also be used for an analysis discriminating between particles based on particle absorbance.

A. Devices and Methods for Measuring Fungal to Microbial Ratios Using Particle Size 1. Devices Devices for detecting particles of various sizes include microscopes, flow cytometry devices, particle counters, dynamic light scattering apparatus, and laser diffraction apparatus. The devices may include microscopes set up for brightfield or fluorescent imaging. Other devices may include image capture and image processing devices that process microscopy images, or flow cytometry data analyses.

Devices for detecting particles of various sizes are well known in the art. The devices are routine in most laboratory settings, and some are adapted for field use, such as field microscopes and portable dynamic light scattering instruments (Maurer-Spurej et al, Phys Med Biol.,51(15):3747-3758 (2006)).

2. Methods

Typical methods for detecting particle size include of light microscopy, fluorescent microscopy, flow cytometry, particle counting, dynamic light scattering, and laser diffraction.

The methods may include individual counts of particles of different sizes, or counts of particle number and particle areas. The methods may include a sum of all particle areas for detected particles. The detected particles may be measured at less than about 10 μm², such as between about 0.5 μm² and about 10 μm², and these define as the bacterial fraction in a test sample. The detected particles may be measured at greater than about 10 μm², such as between about 10 μm² and about 800 μm², and these define the fungal fraction in a test sample.

The methods may include comparing the number of particles measuring greater than about 10 μm², and the number of particles measuring less than about 10 μm² to obtain the fungal to bacterial fraction in a sample.

The method may include comparing the total area from the particles measuring greater than about 10 μm², and the total area from the particles measuring less than about 10 μm² to obtain the fungal to bacterial fraction in a sample.

The method may include comparing the total volume from the particles measuring greater than about 20 μm³, and the total area from the particles measuring less than about 20 μm³ to obtain the fungal to bacterial fraction in a sample.

B. Devices and Methods for Fungal to Microbial Ratios Using

Particle Absorbance or Color

1. MicroBIOMETER ® Devices

The Microbiometer devices include membranes, which may be enclosed and/or pretreated membranes, extraction fluid, membranes, and whisking devices, for accurate detection of soil microbial load. In some forms, the membranes are enclosed in a package. The package may include a sample window presented by one or more openings for sample application.

The seal around the sample window restricts movement of microbes past the window. The package may also include a quality control window presented by one or more openings for quality control of the detection process.

The membrane retains the microbes on the surface providing a colored sample and allowing the intensity of the color in the window to be used to estimate microbial biomass, thus it is important that microbes not migrate outside the window perimeters. In a preferred embodiment the membrane is enclosed in heat laminated material. This process ensures a secure seal around the window which retains microbes in the window area and at a thickness of about 10 mil (thousandths of an inch) is sufficiently firm to prevent casual bending that would break the seal around the window. Heat laminating materials such as those provided by Uline contain an adhesive that does not migrate except at high temperatures which is a prerequisite for the device as adhesive that migrates can block the pores of the membrane and inhibit the passage of fluid into the membrane.

The strip device can be utilized in two ways: it can be dipped or have sample applied to the window. If it is dipped the strip has to contain a volume of membrane that will only absorb the desired amount of fluid. Alternatively, the strip can have a test window with an indicator such as a color change or disappearance that indicates sufficient fluid has been absorbed. In the case of a dipstick, each test is an individual strip. In the case of a strip to which sample is added, e.g. by pipette, the strip can be a membrane of almost any volume to which a measured amount of sample is added to the window. In this case the membrane can be packaged with one or more windows and/or quality control windows. The laminated strip can have a label on the top that contains instructions for application of sample and indicates window positions. The laminate can be in the form of pouches or rolled film and lamination should be performed according to laminating instructions provided by the laminator and laminating material. The membrane used for the test must be heat resistant so that pore size and structure is not adversely affected by the process. Fiberglass membranes sold as pre-filter material by DSC Data Service Corporation or LIS Laboratory Instrument Services serve well for lamination: they have the correct pore size, they are wettable, they are not adversely affected by lamination and they remain functional for long periods as evidenced by accelerated stability testing at 70 C. For optimal performance the side of the membrane exposed by the window should be as smooth as possible. The DSC membrane has a rough and a smooth side. The windows of the strip can be only on one side of the laminate or on both sides. In a preferred version the window/s is only on one side as this prevents the tester from wetting the strip if it is placed on a wet surface.

a. Membranes

The membrane surface exposed in the window should be as even as possible to provide even distribution of the microbes. Devices include fluid-absorbable membranes, typically, sheet-like membranes of any desired geometric shape and dimension. The sheet-like membranes are typically thin membranes that can be cut to a desired width and length. The membranes may be precut to a desired width or length, or can be provided as membrane sheaths for cutting by the end user to the desired geometric shapes and dimensions. For example, the membrane is cut to a 2.5 cm square, but other dimensions are contemplated. The size of the membrane can be adjusted to increase or decrease the amount of fluid it can absorb and thus increase or decrease the level of detection/sensitivity.

The membrane should be selected so that it is not stained by soil pigments and does not bind other particles than the microbes of up to 200 micrometers present in the extraction fluid.

In a preferred embodiment, the membrane is a fiberglass membrane enclosed in a heat laminated device. Heat lamination materials contain adhesives that only migrate at very elevated temperatures, ensuring that the functionality of the membrane will not be compromised by adhesive seepage over time. Heat laminated devices have the advantage of securely sealing the area around the sample window so that microbes are retained on the surface of the membrane window only. For example, a 10 mm laminating material provides a sturdy support for the membrane a secure seal around the window and very cheap device. The seal around the membrane window must be secure, otherwise microbes will migrate on the surface of the membrane beyond the window and the intensity in the window will be lower than it should be.

Membranes are typically made from natural or synthetic polymers. The membranes may also be made of a combination of natural and synthetic polymers. Suitable polymers include fiberglass, anopore (ANP), cellulose acetate (CA), cellulose nitrate (CN, nitrocellulose), nylon/polyamide (NYL), polycarbonate (PC), polyethersulfone (PES), polypropylene (PP), regenerated cellulose (RC). In preferred embodiment, the membrane is fiberglass because it is resistant to the high temperature used in heat lamination is wettable and does not generally bind the pigments in soil.

Examples of suitable fiberglass membranes include DSC and LIS fiberglass prefilter material and WHATMAN® glass microfiber filters of the following grades: 934-AH®, GF/A, GF/B, GF/C, GF/D, GF/F, GMF, GF, and LIS, with or without binders. Binders may be organic or inorganic.

The membranes are fluid-absorbable. Typically, the fluid is an aqueous fluid containing between about 75% and 99% water. For example, the fluid absorbed by the membrane may contain about 60%, 65%, 70%, 75%, 80%, 85%, 90%, and 95% water. The water of the aqueous fluid can be stream water, tap water, purified water, filtered water, deionized water, or distilled water.

Membranes in an aqueous environment have an attractive or repulsive response to water. The material composition of the membrane and its corresponding surface chemistry determine the interaction with water, thus affecting its wettability. Typically, the membranes are made of hydrophilic material. Hydrophilic materials are characterized by the presence of active groups that have the ability to form "hydrogen-bonds" with water. The wettability of the membrane can be enhanced by detergent and other substances in the extraction fluid.

Typically, the membranes retain microbes with a size (diameter) between 0.5 micrometers and 200 micrometers. Soil pigments smaller than 1µm are not retained. These membranes are porous, with a pore diameter of between about 1 micrometer and 10 micrometers. Microorganisms larger than 1-2 micrometers in diameter are retained on the surface of the membrane by the membrane pores or adhesion to the fiberglass. Typically, the membranes include pore sizes having an average diameter from between 0.5 micrometers and 20 micrometers. For example, the membrane pore size is from between 0.5 micrometers and 10 micrometers.

The membrane is able to absorb sufficient extraction fluid to capture a significant quantity of microbes to stain the sample window. The membrane has a volume that allows absorption/retention of a minimum volume of extracted soil sample with microorganisms suspended therein for accurate determination of the microbial load. Suitable membrane depth is from between 0.1 mm and 10 mm, but preferably is between 0.1 mm and 2 mm. Suitable volumes of extracted soil sample that can be applied to the membrane devices for accurate determination of microbial load of the soil include average volumes of between 100 µl and 1 ml. For example, the volume of extracted soil sample that can be applied to the membrane devices for accurate determination of microbial load of the soil includes volumes of between 50 µl and 1000 µl.

b. Anti-Foaming and Clarifying Agents

Anti-foaming agents act by decreasing the surface tension of gas bubbles and reducing foam. Exemplary anti-foaming agents include alcohols, stearates, insoluble oils, polydimethylsiloxanes, other silicones and glycols. Anti-foaming agents can prevent the formation of foam or can be added to disperse a foam that has formed. Anti-foaming agents can be added as a measured amount of dry powder, or as a tablet. One example of an anti-foaming agent is poly(dimethylsiloxane), the silicon dioxide simethicone. An exemplary concentration of simethicone is 125 milligrams of simethicone in a volume of 25 mL or 5 milligrams per mL solution. For example, an anti-foaming agent is present, such as CAPSIL®.

In one embodiment, a clarifying agent is added to a final concentration of about 50 -150 ppm or final CLOROX® concentration of 10%.

A releasing agent such as CAPSIL® may also be added to the soil sample in the reaction vial. For example, CAPSIL® may be added to a final concentration of 0.2%. CAPSIL® is a 100% active blend of organo-silicone and non-ionic surfactants that enables solutions to spread, sold by Aquatrols, NJ. CAPSIL® is not stable when diluted in clarifying reagent but 0.1% TWEEN®® gives the same result and is stable in the diluted reagent.

For example, a single tablet of a clarification agent and a single, measured drop of releasing agent are added to 200 ml-400 ml of solid soil or 2 mL of compost extract in the reaction vial immediately prior to the addition of water and shaking. Alternatively, 5×50 µl drops of a saturated solution of Chlorine Dioxide and a 20 µl single drop of CAPSIL® are added to 200-400 ml of solid soil or 1-2 mL of liquid soil in the reaction vial immediately prior to the addition of 10 ml water and shaking. 10 mL of a premixed solution of clarifying and releasing agent consisting of 0.08 mg/mL Chlorine Dioxide and 0.1% TWEEN® 20 may be provided in the reaction vial.

Anti-foaming agents can be used to prevent or reduce the formation of bubbles resulting from agitation. Anti-foaming agents such as the silicon dioxide simethicone can be added according to the requirements of the sample. For example, simethicone is added to a final concentration of 5 milligrams per ml. Anti-foaming agents can be added prior to shaking to prevent formation of foam, or can be added after shaking to disperse foam that has formed, according to the requirements of the sample. The mixture of soil samples including releasing agents, clarification agents and/or anti-foaming agents are solubilized by the addition of tap water to the reaction vial. For example, water is added to the reaction vial to a total volume of 10 mL. Water can also be added to a total volume of less than 10 mL, such as to make a total volume of 1 mL, 2 mL, 3 mL, 4 mL, 5 mL, 6 mL, 7 mL, 8 mL or 9 mL, according to the requirements of the operator. Sufficient water can also be added to a final volume of more than 10 mL, such as to up to 25 mL, or more than 25 mL.

c. Exemplary Method

Immediately following the addition of water, the reaction vial cap is screwed onto the vial and the contents are mixed by vigorous agitation.

Agitation can be manual (i.e., shaking by hand, for example, in a vertical and/or horizontal plane), or can be assisted by the use of an automated agitation device, such as a vortex shaker ("vortexing"), sonication or a device similar to a ROBART® Shaker device or by a vibrating probe.

The amount of agitation required to dissociate microbes from soil particles varies depending upon the nature and quantity of the sample and depending upon the method of shaking. Vigorous shaking by hand for 10 to 20 minutes can be sufficient to release microbes from 200-400 ml of solid soil or 2 mL of liquid soil into 10 ml of solution in the absence of releasing agent. In the presence of a releasing agent such as 0.2% CAPSIL® 5-20 minutes of agitation by hand shaking or 1 minute of agitation using a ROBART® shaker, or 10-20 seconds of a vibrating probe should be sufficient to release the microbes from 0.2-0.5 ml of solid soil or 1-2 mL of liquid soil.

Immediately following agitation, the vial is placed vertically in a rack with the cap facing upwards. The cap is removed from the reaction vial and the solution is allowed to settle for up to 20 min.

The method for determining the microbial load of a soil requires: a soil sample;

A soil sampler capable of delivering a set volume of sample an extraction fluid;

agitation devices (optional);
pipette (optional); and
a membrane device, such as the MicroBiometer™ and color intensity gray scale or colored strip or cell phone app, or a colorimeter.

Generally, the method includes reconstituting the soil sample in the extraction fluid so that the microbial biomass of the soil is released from the soil particles and enters the extraction fluid. The extraction fluid with the extracted microorganisms suspended therein (extracted soil sample) is then pipetted into the sample window of the membrane device, or the membrane is dipped into the extraction fluid.

An exemplary test card is shown in FIG. 4A. A portable device with a processor and an image capture device, such as a mobile phone, a personal digital assistant, portable computer, or a tablet, having suitable image processing capability, may be used to detect the fungal fraction, the bacterial fraction. The process typically includes a software or an application that detects the light intensity from the color scale or the gray scale of the device. The portable device generally provides the fungal to bacterial ratio from the test card sample window containing a measured amount of soil extract.

2. Measuring Fungal and Bacterial Fractions using Spectrophotometry or Colorimetry Microbial biomass is estimated by spectrophotometric assay of the extracted solution or by the membrane method. If estimated by the membrane method, it can be analyzed visually or by cell phone grey scale app. The test is read by comparing the intensity of the sample site to a gray scale which allows one compensate for the various pigments in different soils (yellow, red, gray brown): using a gray scale through a red (or other) filter allows one to detect color intensity not color itself. Analysis of the pigmented intensity by grey scale, compensates for the various pigments. The red filter can be a photographic quality clear red sheet applied to the label or one can use a gray scale with red lens glasses. It is also possible to use other colored filters. By cell phone app, the color of the sample is read as a correlate of absorbance. The membrane is white, giving a value in all three channels close to the maximum of 255. Deposition of colored particles obscures the white membrane, and the difference between the color measured in each of the three channels (red, green, and blue) and 255 correlates with particle density, because the light that would normally be reflected off the white membrane is now absorbed by the particles. Fungi and bacterial have different absorption spectra which allows their contribution to the total microbial biomass to be differentiated.

Figure 4B:
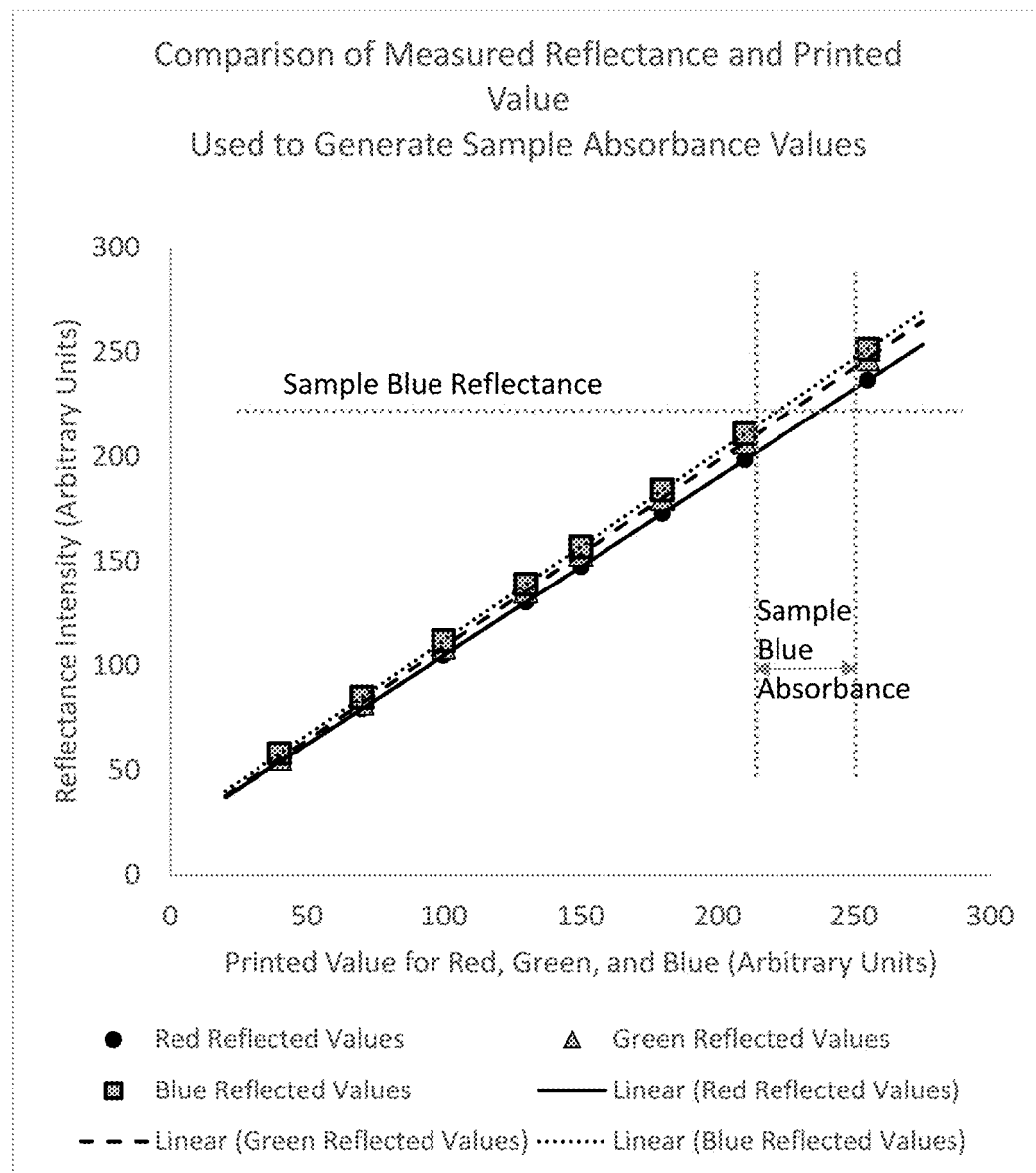
FIG. 4B is a graph showing a sample reflectance (intensity) at three different light wavelengths (red, green, and blue channels corresponding to illumination with light at wavelength between about 600 nm and about 650 nm for red channel, between about 500 nm and about 570 nm for the green channel, and between about 400 nm and about 450 nm for the blue channel) as compared to comparator reflectance (intensity) at the three different light wavelengths. The comparator reflectance from one color scale disk forms a calibration line. The value on the x-axis where the horizontal line crosses the calibration line is taken as the sample intensity for that channel.

The absorbance of the particles in the red, green and blue channels is defined by where they cross the line fitted to the red, green, and blue reflectance of the color or grayscale surround colors, where the y-values are the reflectances and the x-values are the values of the corresponding printed color or grayscale comparators. This crossing point is extrapolated to the equivalent printed surround color as determined by the fitted line, which corrects for differences in ambient lighting, because the x-axis extrapolation of the crossing point is nearly identical in different lighting conditions. This is shown in FIGS. 4A and 4B.

The gray scale may not only be in the form of color strips. The gray scale strips may be in any form: chart, strip, color discs, or have digital values for the color shades to aid with electronically establishing the soil microbial load. Electronic forms of the gray scale colorimeter may be provided as smart phone applications. The electronic form of the gray scale colorimeter may read the intensity of the membrane strip at the sample window using the end user's cell phone and estimate microbial biomass using a curve.

After the sample has been analyzed using the MicroBIOMETER® gray scale strips, it is possible to analyze the same extraction fluid using a filter tube and get a colorimeter reading.

An exemplary method typically includes:
a) applying a measured amount of soil extract to the sample application site of the device, such as the device 10;
b) detecting the particle absorbance from the sample application site at a light wavelength between about 600 nm and about 650 nm;
c) detecting the particle absorbance from the sample application site at a light wavelength between about 400 nm and about 490 nm;
d) and applying the particle absorbance in b) and the particle absorbance in c) to equation 1 to obtain the fungal to bacterial ratio:

$$R = a - (a^2/b) \quad \text{(equation 1)};$$

wherein
R is fungal to bacterial ratio;
a is particle absorbance at a light wavelength between about 600 nm and about 650 nm; and
b is particle absorbance at a light wavelength between about 400 nm and about 490 nm.

Generally, the method also includes for steps b) and c):
measuring reflectance from each comparator of the color scale or gray scale strip at the light wavelength to obtain a calibration line; and measuring reflectance from the sample application site and the same light wavelength; and
obtaining the particle absorbance from the sample application site for the light wavelength from the calibration line.

An exemplary calibration line is presented in FIG. 4B. A soil extract's reflectance value at three different channels is obtained when the soil extract is placed on the sample application site, such as at the sample application site 12 on the device 10, and the reflectance at the three different channels is obtained by the portable device for each one of the comparators, such as comparators 16, and from the sample application site.

The comparator's reflectance from the three different channels forms a calibration line for that channel from which the sample reflectance or absorbance for that channel is obtained.

3. Light Wavelengths and Channels

Generally, the particle absorbance may be measured at light wavelengths of the visible spectrum and infrared wavelengths. The absorbance may be measured at light wavelengths between about 380 nm and about 750 nm, such as between about 400 nm and about 450 nm, between about 450 nm and about 500 nm, between about 500 nm and about 550 nm, between about 550 nm and about 600 nm, between about 600 nm and about 650 nm, between about 650 nm and about 700 nm, between about 700 nm and about 750 nm.

Individual wavelengths that may be used include wavelengths of about 400, about 450, about 500, about 550, about 600, about 650, about 700, or about 750 nm, preferably about 430 nm, about 550 nm, about 635 nm, or about 700 nm.

Light wavelengths between about 380 nm and about 410 nm represent the ultraviolet channels, between about 410 nm and about 485 nm represent the blue channel, between about 485 nm and about 570 nm represent the green channel, between about 570 nm and about 590 nm represent the yellow channel, between about 590 nm and about 620 nm represent the orange channel, and between about 620 nm and about 700 nm represent the red channel. Wavelengths above about 750 nm and up to about 1064 nm represent the infrared channel.

C. Portable Devices, Software, and Applications

The portable devices may be used to detect reflectance or absorbance from the sample application site and from the comparators. The portable devices are typically equipped with software or an application that calculates the light intensity from the comparators, forms the calibration line, and provides the intensity value for the sample at the sample application site.

The portable devices typically include a processor and an image capture device.

The processor may be configured to measure the color or light intensity. The portable device may communicate wirelessly with a remote processing device, such as a central computer, for storing color or light intensity and/or calculating the test result. The portable device may be configured to transmit the data to the remote processing device, and receive and output the calculated test result.

The remote processing device may be adapted to store one or both of the data and the test result. The remote processing device may be adapted to store one or both of the data and the test result from a plurality of assays or portable devices.

The portable device or the remote processing device may be configured to process the data and the test result from a plurality of assays or portable devices to calculate one or more group values or parameters, such as an average, a standard deviation value, a trend function or the like. The processor may be adapted to output the group value or parameter.

The portable device may be configured to modify the image to optimize the color representation of the image.

The portable device may be configured to apply correction and/or filtering to an image to remove electronic or optical noise from the image. The portable device may be configured to discard irrelevant portions of the image to reduce processing time. The processor may be configured to reject images which are of inadequate quality.

The processor may be adapted to convert a color image to a grey scale image or to a black and white image.

The processor may be adapted to summate one or more values of pixels in an identified region of interest.

The portable device may be configured to transmit and/or store associated data along with the data. The associated data may include one or more of: a date or time of image capture; geolocation data for the performed assay; image capture device settings; reagent data; and user generated data. The user generated data may include spreadsheet or database data, image or sound files, typed or written text or the like.

The portable device may be adapted to display instructions or guidance to the user for performing the test and/or interpreting the test result. The portable device may be adapted to provide substantially real time feedback to the user during image capture. The feedback may relate to one or more of the position, orientation, and settings used. The portable device may be configured to automatically capture the image.

The image processing software on the device is provided as what is commonly described as an "App". Ancillary software can be integrated with the image processing to facilitate the use, record keeping, or storage of the results.

Results from assays can be quantified and/or recording using the mobile phone simply by providing the image processing software.

The app and the software are typically configured to obtain the intensity values from the sample application site and display these values on a monitor or screen of the portable device. The app or software may also calculate the fungal to bacterial ratios using equation 1 and display this ratio on a monitor or screen of the portable device. The values may be stored in the portable device, and/or communicated to another device.

Portable devices with spectrometric capabilities are in use and may detect visible, ultraviolet, as well infrared and near infrared spectra (Ghas semi et al., *IEEE Trans Biomed Eng.* 64(7): 1650-1653.(2017); McGonigle et al., *Sensors,* 18, 223 (2018); and Burggraaff et al., *Opt Express.;* 27(14):19075-19101 (2019)).

IV. Kits

Kits containing extracting fluid, optionally, providing the extraction fluid as a powder, and a test card and instructions for use are provided. The kits may also include a pipette, a whisker, a whisker probe, a soil sampler, matte brown imaging background, a measuring vessel for water, and a tube for extracting. The kits may also include instructions to software for use with a portable device and the extraction fluid.

The present invention will be further understood by reference to the following non-limiting examples.

EXAMPLES

Example 1

Measurement of Fungal:Bacterial Ratio by Digitized Microscopy

The test and device described in U.S. Pat. No. 10,179,926 estimates the concentration of soil-colored microbes between 1 and 100 µm in size in a soil sample that has been immobilized on a membrane. The digitized microscopic method and process herein measures the total microbial biomass (MB), the fungal fraction in the MB, the bacterial fraction in the MB, as well as the ratio of fungal to bacterial fractions.

Materials and Methods

Processing of Soil Samples

A soil MB extract was prepared from a variety of soils using the following procedure.

A fresh field moist soil sample was sieved to 3 mm. Sieving improves

CVs.

The microBIOMETER packaged extraction powder was poured into the microBIOMETER tube.

9.5 ml of water was measured out in the microBIOMETER measuring cup and added to the tube.

The extraction powder was dissolved by shaking or whisking.

½ cc of soil was tightly packed into the microBIOMETER soil sampler and added to the tube.

If the soil was too compacted, e.g. a clay soil, a spatula was used to break it up before whisking.

The contents of the tube were whisked by placing the microBIOMETER whisker with the microBIOMETER probe on the tube and whisking for 30 seconds. It was important that the whisker not be too strong or too weak and that the probe reach the bottom of the tube.

The tube was allowed to sit on non-vibrating surface for 20 minutes.

3 aliquots of 14 µl of extract were placed on a microscope slide and covered with cover slips.

10 images taken in a spiral pattern moving from the outer edges of the coverslips toward the center were made from each coverslip. The 30 images were digitally analyzed to determine the areas of individual particles and the total area of all the particles, using a predetermined scale of 8.1 pixels/µm.

Generation of F:B Ratio from Digitized Microscopy

The digital microscopic analysis produces a total area of all the particles in the microscopic field. It also generates a list of areas that are sorted by size. Since the largest reported soil bacteria are 2×5 µm (Portillo, M. C., Leff, J. W., Lauber, C. L. Fierer, N. (2013). Cell Size Distributions of Soil Bacterial and Archaeal Taxa, Applied and Environmental Microbiology Volume 79 Number 24 p. 7610-7617), all particles were sorted by area and classified by size.

Those less than or equal to 10 µm$^2$ were classified as bacterial.

Those larger than 10 µm$^2$ were classified as of fungal origin.

Confirmation that large particles were indeed fungal was achieved using a standard fungal stain, lactophenol blue (Leck, *Community Eye Health*, 12(30):24 (1999)). When extracted microbial biomass was incubated with lactophenol blue (Carolina Biological) at ratio of 5:1, the fungal structures remained in the grape-cluster or coil-like formation but were blue, and the much larger fungal (20 to 800 µm$^2$) structures could easily be distinguished from non-fungal.

To generate various fungal concentrations for experimentation, soil MB extracts of 8 different soils were generated as described above. Fungi were concentrated by centrifuging 4 tubes with 1 ml of the resulting microbial extraction fluid for 3 minutes at 1000 rpm in a microcentrifuge, producing a film of fungi on the side of the tube. For each tube, either 200, 350, 500, or 650 ul of the centrifuged liquid was removed carefully to not disturb the fungal film, and the fungi were resuspended by vortexing. The removed centrifuged supernatant was saved and examined microscopically and showed very decreased fungal concentrations. Using this method, up to 6 different fungal:bacterial ratios were generated for each soil.

For each sample, three 14 ul aliquots were placed on a microscope slide and each covered with a slip. Images of 10 microscope fields/cover slip were obtained according to a spiral pattern that progressively moved toward the center of the coverslips, for a total of 30 microscope images. Particles were detected by binarizing the image with a threshold, and the areas of the particles determined by finding the area of the polygon that circumscribed each discrete particle. The areas of the particles for all images were combined and sorted by size. All particles with area less than 10 µm$^2$ were categorized as bacterial, and all larger particles were categorized as fungal. The sums of the areas of all bacterial and fungal particles were calculated separately for each microscopic field and the averages over all fields calculated. The ratio of the average area of the fungal particles to the average area of the bacterial particles yields a fungal:bacterial ratio that can then be used to calculate the percent contribution each makes to the total microbial biomass. For example, a fungal:bacterial ratio of 1 means that 50% of the microbial biomass is fungal and 50% is bacterial. If the ratio is 3, then 75% is fungal and 25% is bacterial.

It should be clear to anyone skilled in the art that the extraction process also enables flow cytometry as it is a method that can analyze the extracted microbes by size and shape in the same manner as digitized microscopy.

Results

Figure 1A:
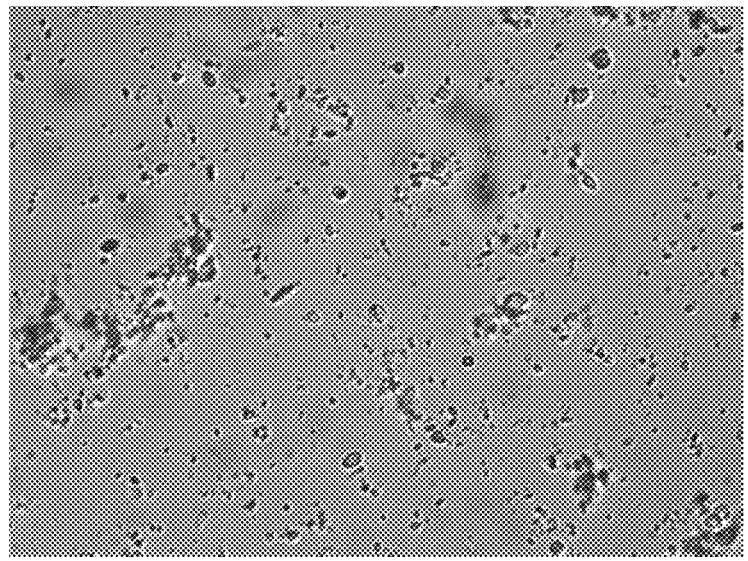
FIGS. 1A and 1B are photomicrographs of soil analyses.
Figure 1B:
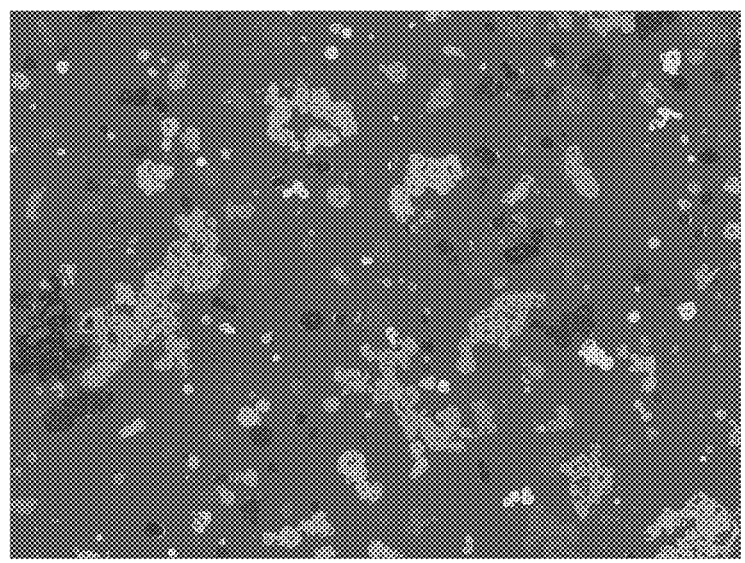
Figure 1C:
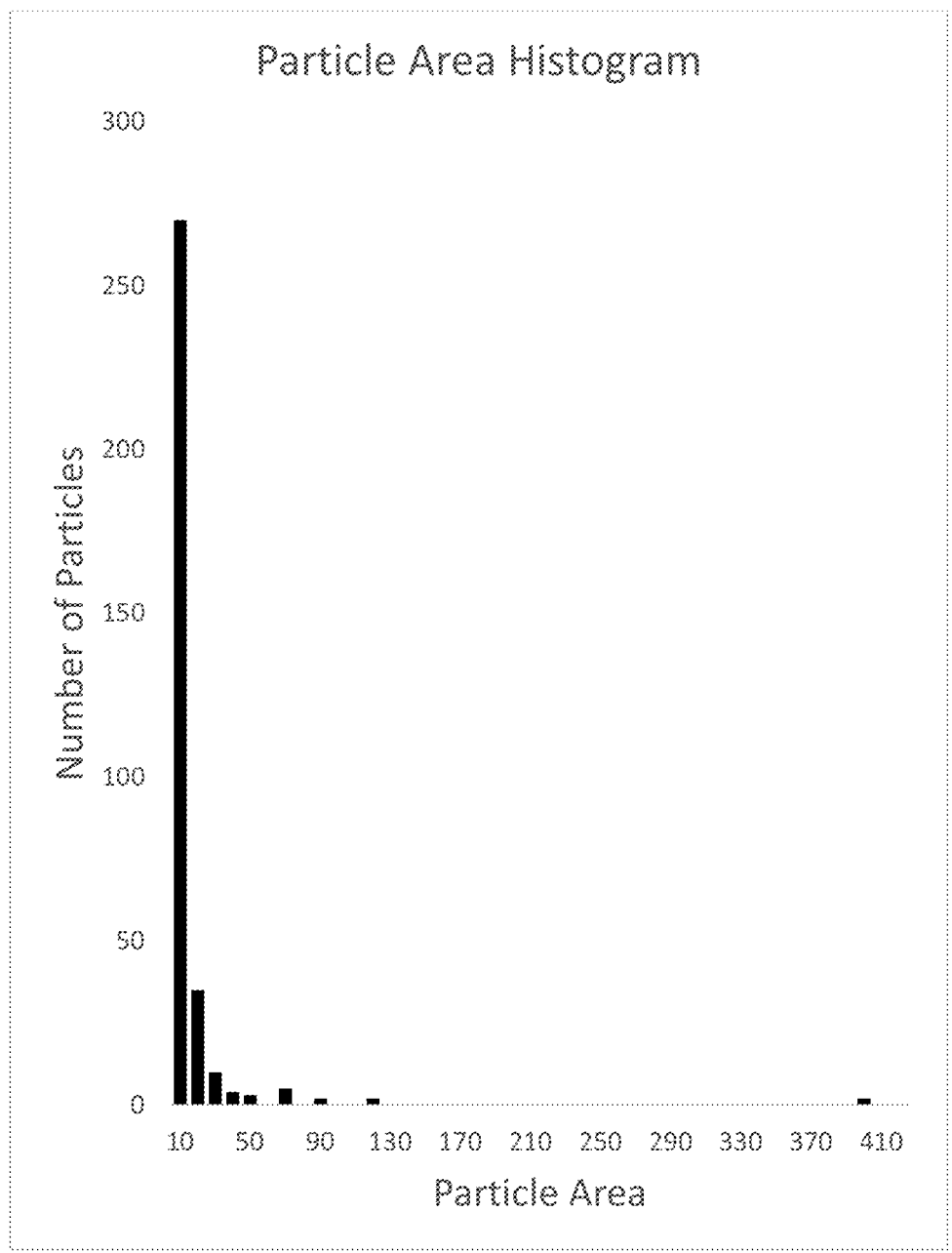
FIG. 1C is a graph showing the number of particles in a sample separated by their size (Particle area ($\mu m^2$)). The particles are presented in two groups—one with size greater than about 10 $\mu m^2$ in size and the other with size less than about 10 $\mu m^2$. From FIG. 1C the combined area for each group of particles can be determined. The summed area for the smaller particles is 675.37 and for the larger particles is 1733.81. The fungal to bacterial ratio as a ratio of summed area of fungal particles over summed area of bacterial particles. The fungal area to bacterial area was 2.57.

Results are shown in FIGS. 1A (original image) and 1B (image after it has been segmented into individual contiguous particles, with adjacent particles in different intensities). The area of each particle was determined by the area of the polygon that circumscribed it, or more simply by the number of pixels it consumed. Both methods produced similar results. The total area of all particles was calculated for each of the 30 images and averaged.

Figure 2:
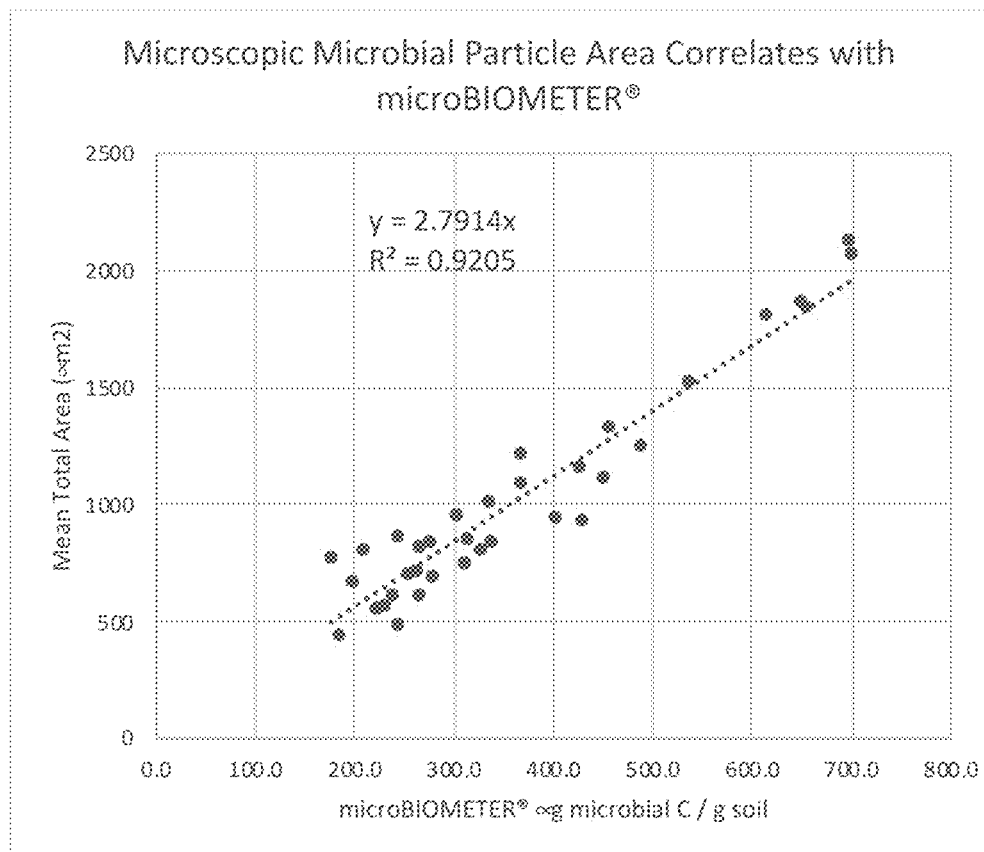
FIG. 2 is a graph of the correlation of the analysis of 35 soils analyzed by digital microscopy and then compared to the average microbial biomass result obtained with the test card device sold as microBIOMETER® described in U.S. Pat. No. 10,179,926.

When 35 soils were analyzed by digital microscopy and then compared to the average microbial biomass result obtained with the test card device (sold as microBIOMETER®) described in U. S. Pat. No. 10,179,926, the correlation is excellent, as shown in FIG. 2. This high correlation indicates that the areas that the microbes cover in the microscopic analysis is analogous to the area of the sample window that microbes obscure in the microBIOMETER® test.

This analysis gave fungal:bacterial ratios from 0.2 to 8, in-line with manual microscopic analyses described in the literature (Bailey V. L., Smith J. L. Bolton Jr. H., 2002 Fungal-to-bacterial ratios in soils investigated for enhanced C sequestration. Soil Biol. Biochem 34: 997-1007).

Example 2

Method for Estimating Fungal and Bacterial Populations in a Soil Sample by using MicroBIOMETER® Device and Process and Smart Phone Reader App for Analysis and Generation of Results The test and device described in U.S. Pat. No. 10,179,926 estimates the concentration of soil-colored microbes between 1 and 100 µm in size in a soil sample that has been immobilized on a membrane. The test card/cell phone analysis measures the total microbial biomass (MB), the fungal fraction in the MB, the non-fungal fraction in the MB, as well as the ratio of fungal to bacterial fractions.

Materials and Methods

A soil MB extract was produced as described above in Example 1, sampled using the microBIOMETER® pipette from the top half inch of the extraction fluid, and 3 to 9 drops were applied using the same pipette, which delivers about 30 µl/extraction fluid drop on a window of the microBIOMETER® test card, and the testcard was placed on a brown matte surface (such as cardboard or chipboard) or some other matte surface (can be plastic or wood) which is included in the microBIOMETER® kit and minimizes variation of the readings among different cell phones, and imaging and processing the microBIOMETER® test card with the microBIOMETER® Reader cell phone app ("microBIOMETER® Reader" app by Prolific Earth Sciences Corporation, Montgomery, N.Y.) within 3 minutes to estimate the microbial biomass carbon of the bacteria, Protista, fungi and fungal spores and discriminating between the bacterial and fungal populations based on colorimetric differences.

The microBIOMETER® Reader cell phone app analyzes the microbes bound to the membrane surface in the sample window of the test card and generates numbers in the red, blue and green channels that are comparable to the absorbance of light by the sample in those three color ranges. By measuring the degree to which the white membrane is obscured by the coloration of the sample, the app generates a measurement equivalent to absorbance.

The absorbance of bacteria and fungi differ in the red and blue spectra. Once a sample is read by the app, using a preferred formula:

$$\text{red absorbance} - (\text{red absorbance}^2/\text{blue absorbance})$$

produces a number that correlates with the fungal to bacterial ratio obtained by digitized microscopy as described in Example 1 and can be converted to the microscopically derived ratio. Other algebraic manipulations of the absorbances in the three channels can be used to generate correlations as well.

Results of Colorimetric Determination of F:B ratio

For all soil samples enriched for the F:B ratio, a test card reading generated by subtracting Red from Blue correlated very well with fungal:bacterial microscopic results, with the results of one soil shown in Table 1:

TABLE 1

Colorimetric Determination of F:B ratio

| Soil | Blue-Red | Fungal: Bacterial | Small area | Large area |
|---|---|---|---|---|
| Fungi more concentrated | 81.7 | 3.56 | 3455.43 | 12308.4 |
| Fungi concentrated | 73.7 | 2.8 | 3428.16 | 9610.78 |
| Normal | 65.6 | 1.93 | 3400.73 | 6553.59 |

F:B = 0.1012 (Blue-Red)-4.6939 ($R^2$ = 0.9986)

The slopes of the curve are different for different soils which results in less than optimal correlation of the two methods. By testing different algebraic manipulations of the absorbance numbers generated, it was found that multiplying the blue absorbance—red absorbance numbers by a correction factor of red absorbance/blue absorbance normalized the differences between soils. The fungal:bacterial ratios were calculated from digital microscopy for 45 different samples of various fungal concentrations from 8 different soils with the preferred formula $$\text{red absorbance} - (\text{red absorbance}^2/\text{blue absorbance}),$$

which is equivalent to (blue absorbance−red absorbance)*(red absorbance/blue absorbance).

Figure 3A:
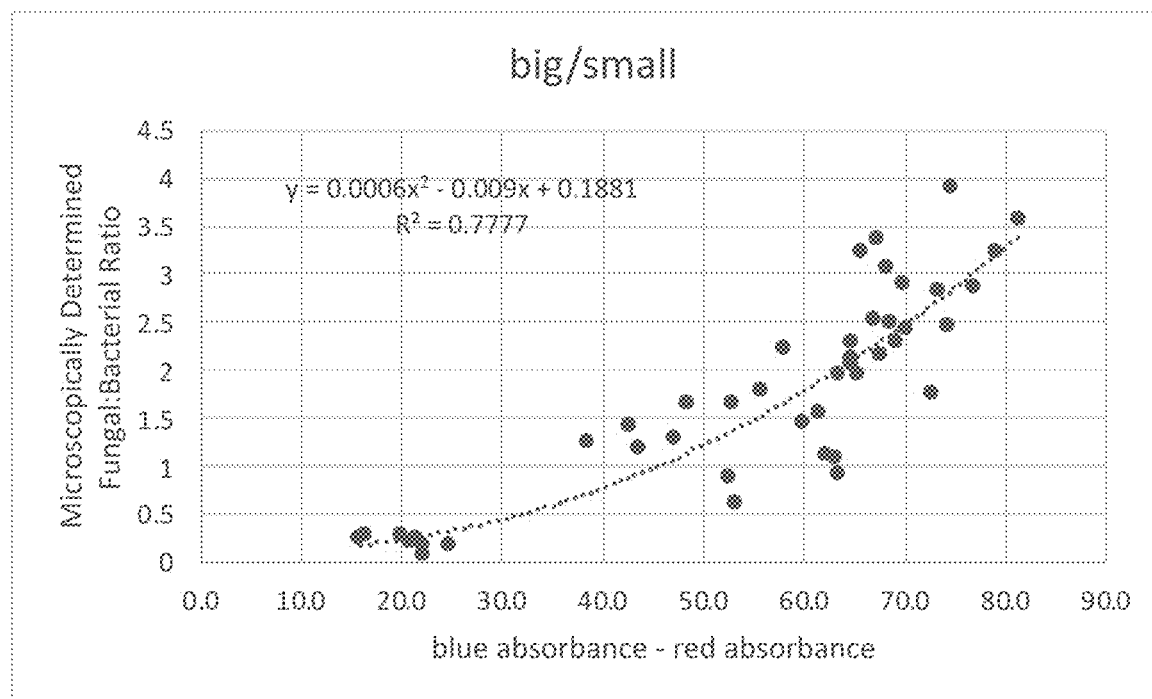
FIG. 3A is a graph of the correlation of Blue absorbance—Red absorbance (x-axis) to fungal to bacterial ratios (y-axis) obtained from digital microscopy for 45 different samples of various fungal concentrations from eight different soils.
Figure 3B:
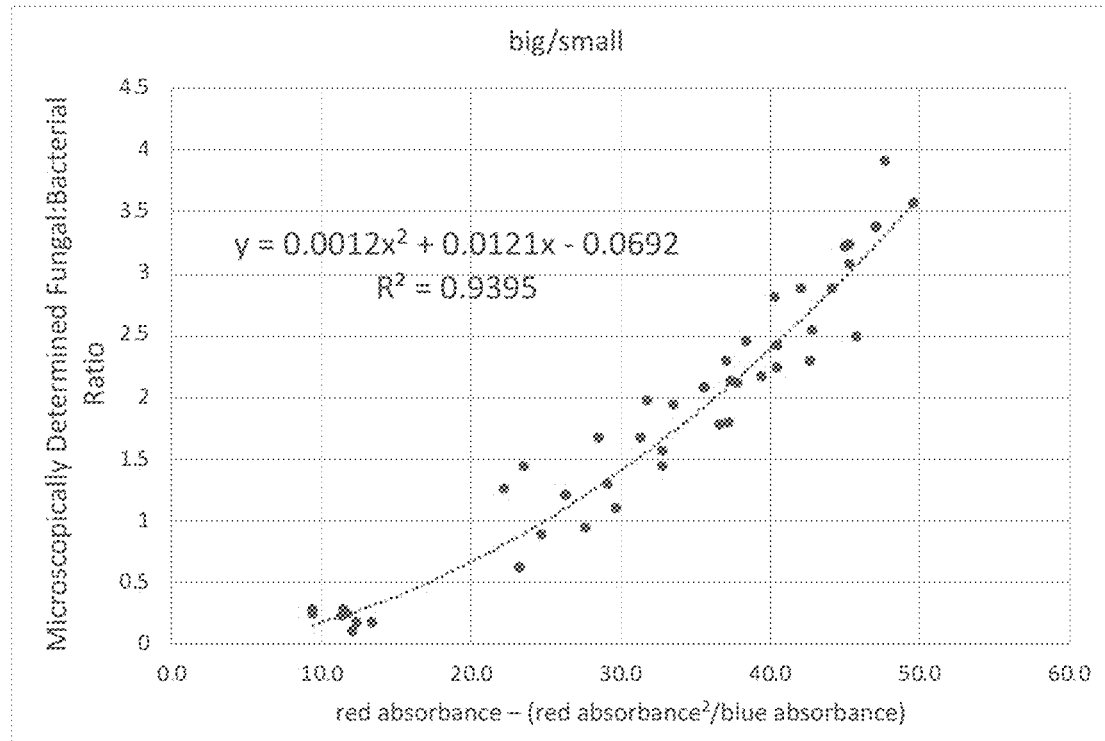
FIG. 3B is a graph of the same 45 samples wherein the differences in slopes found in individual soils was corrected by using the formula red absorbance—(red absorbance$^2$/blue absorbance).
Figure 3C:
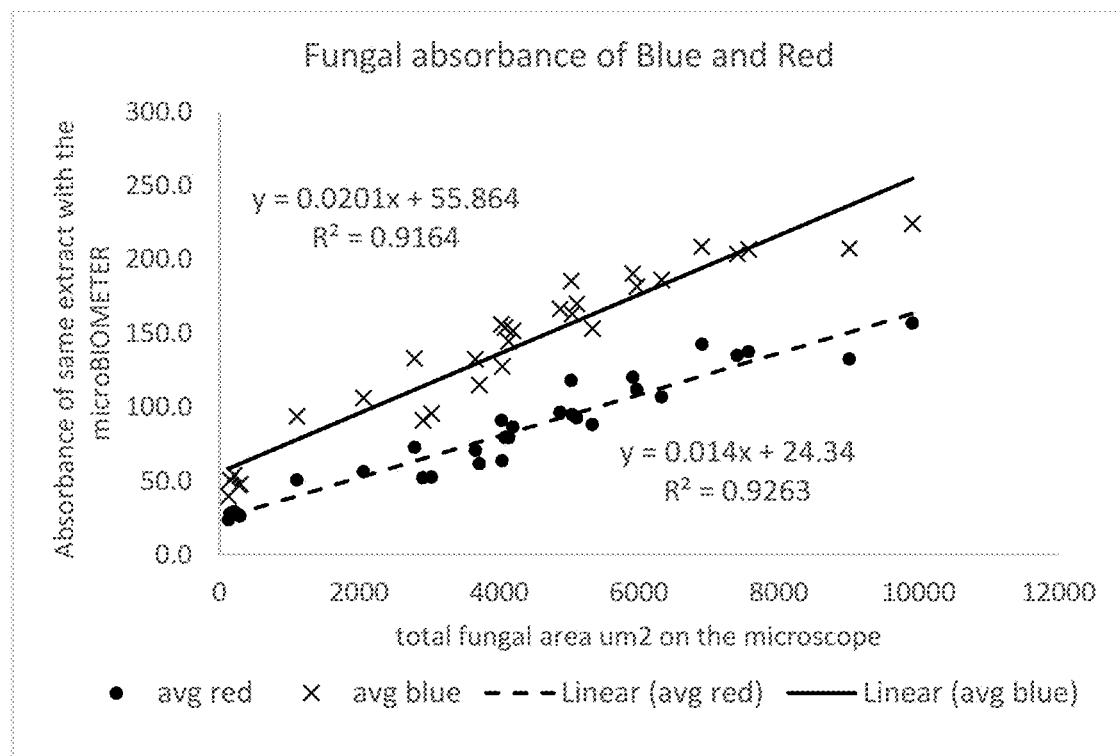
FIG. 3C is a graph showing a correlation between total fungal area ($\mu m^2$) in different soil samples as determined by microscopy and the blue channel and red channel absorbance by the same soil samples as determined using the microBIOMETER test card. The more fungi, the greater the difference in the blue vs. the red absorbance for the microBIOMETER reading for the whole microbial biomass, which includes bacteria as well. Notice how the slope of the line fitted to the blue absorbance is 1.5 times the slope of the line fitted to the red absorbance. Therefore, blue-red increases as fungal fraction, or fungal:bacterial ratio increases.

FIG. 3A is a graph of the correlation of Blue absorbance—Red absorbance and fungal:bacterial ratios from digital microscopy for 45 different samples of various fungal concentrations from 8 different soils. FIG. 3B is a graph of the same 45 samples wherein the differences in slopes found in individual soils was corrected by using the formula red absorbance−(red absorbance$^2$/blue absorbance).

FIG. 3B shows a substantial correlation ($R^2$=0.9395) between the numeric value generated by the smart phone application and the ratio of large (fungal) to small (bacterial) particle volumes by microscopic analysis. This relationship allows the determination of the relative proportions of each component of the total microbial biomass. For example, if the number generated by the app is approximately 40, then the ratio of fungal area to bacterial area is 0.0012*40$^2$+ 0.0121*40−0.0692=2.255. In other words, the ratio is 2.225 fungal to 1 bacterial. With 3.225 total "parts", the percentage of total microbial biomass that is fungal is 2.255/ 3.255=69.3%, and the bacterial percentage is 30.7%. Therefore, one can report the relationship of fungal and bacterial biomass as a number that represents their relative abundance (fungal/bacterial) as well as their percent contributions to the total microbial biomass.

Example 3

Accuracy of the Colorimetric Assay Compared with Eigitized Microscopy

Materials and Methods

Forty-five different F:B ratios were prepared from 8 soil samples that were enriched for F:B ratio as described in Example I.

All soil samples were assayed by digitized microscopy as described in Example 1 and by microBIOMETER®, using 3 drops of soil MB extract.

The F:B ratios were generated for all 45 samples by converting from red absorbance−(red absorbance $^2$/blue absorbance) to the microscopy F:B ratios.

The microBIOMETER® predictions were subtracted from the actual values found by microscopy and the absolute values of the differences were used to create a histogram to judge the accuracy of the app.

Results

The results are shown in Table 2.

More than 90% of the predicted F:B ratios by the microBIOMETER® app were within 0.5 units of the F:B ratio measured by digital microscopy

TABLE 2

Histogram of the absolute value of the differences of the F:B ratios predicted by the microBIOMETER ® assay and the microscopy method for detecting the ratio between fungi and bacteria.

| bins | Frequency | Cumulative % |
|---|---|---|
| 0.1 | 14 | 31.11% |
| 0.2 | 10 | 53.33% |
| 0.3 | 12 | 80.00% |
| 0.4 | 1 | 82.22% |
| 0.5 | 4 | 91.11% |
| 0.6 | 2 | 95.56% |
| 0.7 | 2 | 100.00% |
| 0.8 | 0 | 100.00% |
| 0.9 | 0 | 100.00% |
| 1 | 0 | 100.00% |
| More | 0 | 100.00% |

Example 4

Spectrophotometric Method for Estimating Fungal and Bacterial Populations in a Soil Sample Materials and Methods Soil MB extracts were prepared as described above. 3-5 ml of the extraction fluid was pipetted from the top of the tube into a cuvette for spectrophotometric analysis. Alternatively, a serum filter can be inserted into the tube such that the level of the fluid in the filter tube reaches the level of the rim of the extraction tube to allow the extraction fluid to be poured off into a cuvette for analysis by spectrophotometry and removes any surface debris that could interfere in spectrophotometric analysis.

As described in Example 2, the blue and red absorbance readings are generated and then calculated to give red−(red$^2$/blue), which is then used to calculate F:B based on a calibration equation.

The app uses an expression of light absorbance in its calculations. The redder a sample is, the relatively more blue light is absorbed. The bluer a sample is, the relatively more red light is absorbed. Using a spectrophotometer or colorimeter provides absorbance readings that can be used in a similar manner as the absorbance readings of the app. First the red absorbance (635 nm) is subtracted from the blue absorbance (430 nm). Secondly, an adjustment factor is calculated by dividing the red absorbance by the blue absorbance. The final calculation is (A430−−A635)*(A635/A430) which is equivalent to A635−(A635)$^2$/A430. The colorimeter absorbance readings are linearly corrected to coincide with the absorbance readings produced by the app.

Results

Table 3 shows the raw absorbance readings in two wavelengths for 6 different soils.

TABLE 3

Blue and Red Absorbance of Soil Samples

| soil | a430 | a635 |
|---|---|---|
| 1 | 0.934 | 0.603 |
| 2 | 1.32 | 0.777 |
| 3 | 1.38 | 0.85 |
| 4 | 0.95 | 0.595 |
| 5 | 1.585 | 0.914 |
| 6 | 0.77 | 0.461 |

After correction with the following constants, chosen to get a 1-to-1 correspondence between the colorimeter values and the readings from the app on the membrane, for scale and for offset:

for blue, 57.5 and 64.35, respectively and
for red, 53 and 32.5, respectively,
the correlation between the two methods was determined as shown in Table 4:

TABLE 4

Correlation between the two methods

| Colorimeter A430 corrected | smart phone blue absorbance on membrane | Colorimeter A635 corrected | smart phone red absorbance on membrane |
|---|---|---|---|
| 118.1 | 105.2 | 64.5 | 50.0 |
| 155.5 | 152.4 | 80.9 | 75.7 |
| 140.3 | 151.9 | 73.7 | 87.2 |
| 143.7 | 140.7 | 77.6 | 79.0 |
| 119.0 | 119.8 | 64.0 | 64.8 |
| 108.6 | 115.4 | 56.9 | 62.9 |

$y = 1.004x + 0.0674$
$y = 1.0003x + 0.0038$
$R^2 = 0.4843$
$R^2 = 0.82$

The red−(red$^2$/blue) for the two methods, the microBIOMETER® reader app and the colorimeter, is shown in Table 5:

TABLE 5

The red-(red$^2$/blue) for Soil Samples

| Colorimeter red-(red$^2$/blue) | Smartphone red-(red$^2$/blue) |
|---|---|
| 29.2638564 | 26.2934245 |
| 38.8060896 | 38.0651869 |
| 34.9723386 | 37.1230684 |

TABLE 5-continued

The red-(red$^2$/blue) for Soil Samples

| Colorimeter red-(red$^2$/blue) | Smartphone red-(red$^2$/blue) |
|---|---|
| 35.698904 | 34.6049177 |
| 29.569934 | 29.7363686 |
| 27.0930323 | 28.5943328 |

$Y = 0.9829x + 0.391$
$R^2 = 0.8537$

The slope is essentially unity and the R2=0.8537 is high, higher than the correlations for red or blue alone, shown above.

After converting the red−(red$^2$/blue) to fungal:bacterial for both the colorimeter and smartphone values, the following correlations were determined, as shown in Table 6. The slope is unity and the R2 was ~0.87.

TABLE 6

Correlation between Colorimeter and App predicted f:b

| colorimeter | app |
|---|---|
| 1.23060842 | 0.99346157 |
| 2.16399639 | 2.0821533 |
| 1.75754364 | 1.98036161 |
| 1.83132968 | 1.72080797 |
| 1.25648549 | 1.27066958 |
| 1.05480456 | 1.17494274 |

$y = 0.9912x$
$R^2 = 0.8651$

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific embodiments of the invention described herein. Such equivalents are intended to be encompassed by the following claims.

We claim:

1. A method for measuring a fungal fraction, and a bacterial fraction of a soil microbial biomass in an extraction fluid comprising
   detecting the fungal and bacterial fractions, and fungal to bacterial ratio in a soil extract using particle size and/or particle absorbance,
   wherein particle size larger than 10 μm$^2$ plus or minus 10% defines particles of the fungal fraction, and
   wherein detecting the fungal to bacterial ratio comprises detecting particle absorbance of light at a wavelength between 355 and 470 nm and detecting particle absorbance of light at a wavelength between 550 nm and 700 nm for the particles in the extraction fluid.

2. The method of claim 1, wherein the fungi and bacteria in the extraction fluid are extracted from a soil sample by adding the soil sample to the extraction fluid comprising releasing agents.

3. The method of claim 1, wherein the extraction fluid contains between 8% and 12% NaCl and between 1% and 5% CaCl$_2$.

4. The method of claim 1, wherein particle size is the size of fungal particles and the size of bacterial particles in the soil extract.

5. The method of claim 1, wherein the particle size between 10µm$^2$ and 800 µm$^2$ defines particles of the fungal fraction.

6. The method of claim 1, wherein the particle size smaller than 10 µm$^2$, defines particles of the bacterial fraction.

7. The method of claim 1, wherein the particle size is determined by a method suitable for particle size detection.

8. The method of claim 7, wherein the method suitable for particle size detection is selected from the group consisting of light microscopy, fluorescent microscopy, flow cytometry, particle counting, dynamic light scattering, and laser diffraction.

9. A method for measuring a fungal fraction, and a bacterial fraction of a soil microbial biomass in an extraction fluid comprising
detecting the fungal and bacterial fractions, and fungal to bacterial ratio in a soil extract using particle size and/or particle absorbance,
wherein particle size larger than 10 µm$^2$ plus or minus 10% defines particles of the fungal fraction,
wherein detecting the fungal and bacterial fractions, and fungal to bacterial ratio in the soil extract using particle size comprises:
a) detecting a number of particles in the soil extract with particle size between 10 µm$^2$ and 800 µm$^2$, and counting their total area representing the area from the fungal fraction,
b) detecting a the number of particles in the soil extract with particle size between 0.5 µm$^2$ and 10 µm$^2$, and counting their total area representing the area from the bacterial fraction; and
c) comparing the area in a) with the area in b) to obtain the fungal to bacterial ratio.

10. The method of claim 1, comprising applying the soil extract to a device comprising:
a substrate having one or more sample application sites thereon,
each sample application site comprising a fluid-absorbable membrane,
wherein the fluid-absorbable membrane is wettable by the sample within 5 seconds to 30 seconds of applying the sample, and
wherein the fluid-absorbable membrane retains the soil extract's fungi and bacteria having a size greater than 0.5 µm$^2$.

11. The method of claim 1, wherein particle absorbance is absorbance of stained or unstained fungi and bacteria in the soil extract.

12. The method of claim 1, wherein particle absorbance is absorbance of unstained fungi and bacteria in the soil extract.

13. The method of claim 1, wherein particle absorbance is absorbance of stained fungi and bacteria in the soil extract.

14. The method of claim 13 wherein the instained fungi and bacteria in the soil extract are fungi and bacteria pigmented with soil pigment and without externally applied stains.

15. The method of claim 1, wherein particle absorbance is light absorbance at a light wavelength between 380 nm and 680 nm.

16. The method of claim 1, wherein the particle absorbance is measured with a spectrophotometer, colorimeter, or a portable device with a processor and an image capture device.

17. A method for measuring a fungal fraction, and a bacterial fraction of a soil microbial biomass in an extraction fluid comprising
detecting the fungal and bacterial fractions, and fungal to bacterial ratio in a soil extract using particle size and/or particle absorbance,
wherein particle size larger than 10 µm$^2$ plus or minus 10% defines particles of the fungal fraction,
wherein the fungal and bacterial fractions, and the fungal to bacterial ratio in the soil extract, are determined using equation 1:

$$R=a-(a^2/b) \qquad \text{(equation 1)};$$

wherein
R is fungal to bacterial ratio;
a is particle absorbance at a light wavelength between 570 nm and 680 nm; and
b is particle absorbance at a light wavelength between 380 nm and 470 nm.

18. The method of claim 17, wherein a is particle absorbance at a light wavelength 635 nm; and b is particle absorbance at a light wavelength 430 nm.

19. The method of claim 1, wherein the particle absorbance is compared to a calibration line generated from a color scale or a gray scale.

20. The method of claim 1, wherein the particle absorbance is detected using a portable device comprising a processor and an image capture device, wherein the portable device is selected from the group consisting of a mobile phone, a personal digital assistant, portable computer, and a tablet.

21. The method of claim 10, wherein detecting the fungal and bacterial fractions, and fungal to bacterial ratio in the soil extract using particle absorbance comprises:
a) applying the soil extract to the sample application site;
b) detecting the particle absorbance from the sample application site at a light wavelength between 570 nm and 680 nm;
c) detecting the particle absorbance from the sample application site at a light wavelength between 380 nm and 470 nm;
d) and applying the particle absorbance in b) and the particle absorbance in c) to equation 1:

$$R=a-(a^2/b) \qquad \text{(equation 1)};$$

wherein
R is fungal to bacterial ratio;
a is particle absorbance at a light wavelength between 570 nm and 680 nm; and
b is particle absorbance at a light wavelength between 380 nm and 470 nm;
to obtain the fungal to bacterial ratio.

22. The method of claim 21, wherein detecting the particle absorbance from the sample application site for steps b) and c) comprises:
measuring reflectance from each comparator of the color scale or gray scale strip at the light wavelength to obtain a calibration line; and measuring reflectance from the sample application site and the same light wavelength; and
obtaining the particle absorbance from the sample application site for the light wavelength from the calibration line.

23. The method of claim 1, wherein the method detects the fungal and bacterial fractions, and the fungal to bacterial ratio at ratios between 0.1:1 and 10:1.

24. The method of claim 3 wherein the extraction fluid comprises between 0.0001% and 0.01% of a surfactant.

25. The method of claim 6 wherein the particles are between 0.5 μm² and 10 μm² in diameter.

26. The method of claim 10, comprising applying the soil extract to a device comprising:
- a substrate having one or more sample application sites thereon,
- each sample application site comprising a fluid-absorbable membrane, a sample window, a color scale or gray scale strip, and a quality control window,
- wherein the fluid-absorbable membrane is wettable by the sample within 5 seconds to 30 seconds of applying the sample, and
- wherein the fluid-absorbable membrane retains the soil extract's fungi and bacteria having a size greater than 0.5 μm².

* * * * *